United States Patent
Naito et al.

(10) Patent No.: US 9,598,521 B2
(45) Date of Patent: Mar. 21, 2017

(54) METHOD FOR MANUFACTURING HYDROPHILIC POLYMER PARTICLE

(71) Applicant: Kao Corporation, Tokyo (JP)

(72) Inventors: Kazuki Naito, Wakayama (JP); Shuichi Kaku, Wakayama (JP)

(73) Assignee: KAO CORPORATION, Tokyo (JP)

( * ) Notice: Subject to any disclaimer, the term of this patent is extended or adjusted under 35 U.S.C. 154(b) by 65 days.

(21) Appl. No.: 14/422,975

(22) PCT Filed: Jul. 31, 2013

(86) PCT No.: PCT/JP2013/004648
§ 371 (c)(1),
(2) Date: Feb. 20, 2015

(87) PCT Pub. No.: WO2014/030305
PCT Pub. Date: Feb. 27, 2014

(65) Prior Publication Data
US 2015/0218297 A1    Aug. 6, 2015

(30) Foreign Application Priority Data
Aug. 22, 2012 (JP) .................. 2012-183137

(51) Int. Cl.
| | | |
|---|---|---|
| C08F 220/56 | (2006.01) | |
| A61Q 5/02 | (2006.01) | |
| A61K 8/81 | (2006.01) | |
| A61Q 19/10 | (2006.01) | |
| C08F 2/32 | (2006.01) | |
| A61K 8/02 | (2006.01) | |
| C08F 220/54 | (2006.01) | |

(52) U.S. Cl.
CPC .......... *C08F 220/56* (2013.01); *A61K 8/0241* (2013.01); *A61K 8/8158* (2013.01); *A61Q 5/02* (2013.01); *A61Q 19/10* (2013.01); *C08F 2/32* (2013.01); *C08F 220/54* (2013.01)

(58) Field of Classification Search
CPC ..... A61K 8/0241; A61K 8/8158; A61Q 19/10
USPC ....................... 526/303.1; 510/123
See application file for complete search history.

(56) References Cited

U.S. PATENT DOCUMENTS

| | | | | |
|---|---|---|---|---|
| 2007/0065649 A1* | 3/2007 | Matsui | ................ | C08G 63/183 |
| | | | | 428/220 |
| 2011/0021712 A1* | 1/2011 | Gotou | ................ | C08F 2/32 |
| | | | | 525/319 |
| 2011/0046329 A1 | 2/2011 | Gotou et al. | | |

FOREIGN PATENT DOCUMENTS

| | | |
|---|---|---|
| CN | 102504288 A | 6/2012 |
| JP | 2002-40709 A | 2/2002 |
| JP | 2002-201211 A | 7/2002 |
| JP | 2002-308916 A | 10/2002 |
| JP | 2004-315627 A | 11/2004 |
| JP | 2008-63409 A | 3/2008 |
| JP | 2008-138106 A | 6/2008 |
| JP | 2010-138301 A | 6/2010 |
| JP | 2010-150327 A | 7/2010 |
| JP | 2011-26381 A | 2/2011 |
| JP | 2011-70048 A | 4/2011 |
| WO | WO 2009/096268 A1 | 8/2009 |
| WO | WO 2009/096300 A1 | 8/2009 |

OTHER PUBLICATIONS

Extended European Search Report for European Application No. 13830294.8, dated Feb. 11, 2016.
English translation of the International Preliminary Report on Patentability and English translation of the Written Opinion of the International Searching Authority (Forms PCT/IB/338, PCT/IB/373 and PCT/ISA/237), dated Mar. 5, 2015, for International Application No. PCT/JP2013/004648.
International Search Report issued in PCT/JP2013/004648, mailed on Nov. 5, 2013.

* cited by examiner

*Primary Examiner* — Ling Choi
*Assistant Examiner* — Chun-Cheng Wang
(74) *Attorney, Agent, or Firm* — Birch, Stewart, Kolasch & Birch, LLP

(57) ABSTRACT

In a method for producing hydrophilic polymer particles, a dispersion in which an aqueous-phase component including hydrophilic monomers and a polymerization initiator is dispersed in an oil-phase component including a hydrophobic solvent is prepared. Thereafter, the hydrophilic monomers are polymerized in the aqueous phase by supplying oxygen to a reaction vessel and, while oxygen is being supplied, heating the dispersion having a reduced dissolved oxygen concentration in the reaction vessel so that the temperature of the dispersion is increases. The time from the start of reduction of the dissolved oxygen concentration of the dispersion to the start of the heating is 0.1 hour or more and 3.5 hours or less. The amount of oxygen supplied to the reaction vessel is greater than or equal to 0.02 volume %/h and less than or equal to 0.9 volume %/h with respect to the volume of the dispersion under standard conditions.

14 Claims, No Drawings

METHOD FOR MANUFACTURING HYDROPHILIC POLYMER PARTICLE

TECHNICAL FIELD

The present invention relates to a method for producing hydrophilic polymer particles.

BACKGROUND ART

There is a known method for producing hydrophilic polymer particles by reversed-phase suspension polymerization (see, for example, Patent Document 1). In particular, in producing hydrophilic polymer particles for use in, for example, cosmetic additives, carriers of various chemical substances, and surface modifiers for recording paper, it is important to control polymerization reaction of hydrophilic polymer particles in view of adjusting viscosity and feeling, for example, of a solution of polymer to be obtained.

Patent Document 2 discloses a method for producing polymer fine particles having a substantially uniform particle size in a specific range, specifically a method for producing high-concentration polymer slurry through reversed-phase suspension polymerization by supplying a water-soluble oxidizer and a water-soluble reducer as polymerization initiators to a vinyl monomer aqueous solution and adding a monomer aqueous solution to the obtained slurry for further polymerization. Patent Document 2 also describes a method for deactivating a catalyst with an oxygen-containing gas in order to avoid the influence of a remaining unreacted polymerization catalyst when the polymerization reaction is terminated.

Patent Document 3 shows a method for producing polymerized toner in order to suppress occurrence of odor due to a remaining or liberated chain transfer agent, specifically a method of bubbling a carrier gas in a reaction solution.

Patent Document 4 describes a method for producing toner in which attachment of polymer to a wall surface of a reaction vessel is prevented by introducing a carrier gas into a gas-phase portion of the reaction vessel.

CITATION LIST

Patent Document

Patent Document 1: Japanese Unexamined Patent Publication No. 2008-138106
Patent Document 2: International Patent Publication No. 2009/096300
Patent Document 3: Japanese Unexamined Patent Publication No. 2002-40709
Patent Document 4: Japanese Unexamined Patent Publication No. 2011-70048

SUMMARY OF THE INVENTION

A method for producing hydrophilic polymer particles according to the present invention includes: step 1 of preparing a dispersion in which an aqueous-phase component including hydrophilic monomers and a polymerization initiator is dispersed in an oil-phase component including a hydrophobic solvent having a solubility of 1 mass % or less in water at 25° C.; step 2 of reducing a dissolved oxygen concentration of the dispersion prepared in step 1; and step 3 of polymerizing the hydrophilic monomers in the aqueous phase by supplying oxygen to a reaction vessel and, while oxygen is being supplied, heating the dispersion whose dissolved oxygen concentration was reduced in step 2 in the reaction vessel so that a temperature of the dispersion increases, wherein a time from a start of reduction of the dissolved oxygen concentration of the dispersion in step 2 to a start of heating of the dispersion in step 3 is greater than or equal to 0.1 hour and less than or equal to 3.5 hours, and an amount of oxygen supplied to the reaction vessel in step 3 is greater than or equal to 0.02 volume % per hour and less than or equal to 0.9 volume % per hour with respect to a volume of the dispersion, under standard conditions of a temperature of 25° C. and an absolute pressure of 101.3 kPa.

DESCRIPTION OF EMBODIMENTS

An embodiment will be described in detail below.

A method for producing hydrophilic polymer particles according to this embodiment controls the time, to the start of heating of the dispersion, from the start of reduction of a dissolved oxygen concentration of a dispersion in which an aqueous-phase component including hydrophilic monomers and a polymerization initiator is dispersed in an oil-phase component including a hydrophobic solvent. In this method, the dispersion is heated while being supplied with a predetermined amount of oxygen with respect to the volume of the dispersion. The method for producing hydrophilic polymer particles of this embodiment can stably produce hydrophilic polymer particles having a desired viscosity.

In a polymerization step, in a case where the dispersion is heated with a low oxygen concentration of the dispersion, the concentration of generated radicals reaches a concentration sufficient for starting a polymerization reaction in an early stage, and thus, a polymerization reaction starts at a low temperature. On the other hand, in a case where the dispersion is heated under the same conditions except for a high oxygen concentration of the dispersion, it takes time for the concentration of generated radicals to reach the concentration sufficient for starting a polymerization reaction, and thus, a polymerization reaction starts at a high temperature. As a result, hydrophilic polymer particles produced has a low molecular weight.

In this situation, inventors found that the reaction start temperature can be controlled at a constant temperature by heating the dispersion with a supply of a predetermined amount of oxygen with respect to the volume of the dispersion. However, only adjustment of the amount of oxygen supply in heating causes varies the amount of generated radicals before the start of heating, and thus, it has been difficult to produce hydrophilic polymer particles having a desired viscosity stably. On the other hand, the inventors found that the amount of generated radicals can be controlled by controlling the time until heating of the dispersion starts, and successfully produced hydrophilic polymer particles having a desired viscosity stably by utilizing the control of the generated radicals. None of Patent Documents 1-4 discloses a method for easily producing polymer particles having, for example, a viscosity suitable for applications such as cosmetics and/or cleansing agents by controlling a reaction start time of a polymerization reaction.

Hydrophilic polymer particles produced by the method of this embodiment can be suitably used as an additive for improving feeling of cosmetics and/or cleansing agents in which a small difference in physical properties is supposed to affect the feeling.

(Step 1: Dispersion Preparation Step)

In step 1, an oil-phase component including a hydrophobic solvent is supplied to a reaction vessel. With the oil-phase component is being stirred, the reaction vessel is supplied with an aqueous-phase component including hydrophilic monomers and a polymerization initiator so that the aqueous-phase component and the oil-phase component are mixed.

1. Oil-phase Component

The oil-phase component including the hydrophobic solvent may further include a dispersing agent as a constituent.

(1) Hydrophobic Solvent

The "hydrophobic solvent" herein refers to a solvent whose solubility in water at 25° C. is less than or equal to 1% by mass (mass %).

Examples of the hydrophobic solvent include: a hydrocarbon-based solvent such as hexane, cyclohexane, heptane, octane, benzene, toluene, xylene, and ethylbenzene; halogenated hydrocarbon-based solvents such as carbon tetrachloride and dichloroethane; and solvents based on isoparaffin-based hydrocarbon. Among these substances, in view of chemical properties and ease of handling, the hydrocarbon-based solvent is preferable, hexane and cyclohexane are more preferable, and cyclohexane is much more preferable. The hydrophobic solvent may be a single species or a mixture of a plurality of species.

In view of stability of the dispersion, the amount of the hydrophobic solvent is preferably greater than or equal to one, more preferably greater than or equal to two, much more preferably greater than or equal to four, and yet more preferably greater than or equal to six times by mass as large as the total amount of monomers. In view of productivity, the amount of the hydrophobic solvent is preferably less than or equal to 20, more preferably less than or equal to 17, much more preferably less than or equal to 15, and yet more preferably less than or equal to 10 times by mass as large as the total amount of monomers.

(2) Dispersing Agent

Examples of the dispersing agent include nonionic surfactants, cationic surfactants, anionic surfactants, and amphoteric surfactants. Examples of the nonionic surfactant include: polyhydric alcohol-type nonionic surfactants such as sorbitan stearate, sorbitan palmitate, polyvinyl alcohol, methyl cellulose, ethyl cellulose, hydroxy cellulose, carboxymethyl cellulose, carboxyethyl cellulose, sucrose stearate, sucrose palmitate, and sucrose myristate; and polyethylene glycol-type nonionic surfactants such as polyoxyethylene alkyl ether, polyoxyethylene alkylphenyl ether, and polyoxyethylene polyoxypropylene glycol. Among these substances, in view of dispersion stability, the polyhydric alcohol-type nonionic surfactants are preferable, sorbitan stearate and sucrose stearate are more preferable, and sucrose stearate is much more preferable. The dispersing agent may be a single species or a mixture of a plurality of species.

In view of dispersion stability, the dispersing agent can be a surfactant having a hydrophilic-lipophilic balance (HLB) of preferably 4 to 30, more preferably 5 to 20, and much more preferably 6 to 10. The HLB value can be calculated by "HLB=7+Σ (number of hydrophilic groups)−Σ (number of hydrophobic groups)" according to Davis's formula (see Takashi Takeuchi, "Kaimen kasseizai (Surfactant)," Yoneda Shuppan, 1999).

In view of dispersing the aqueous-phase component in the oil-phase component, the amount of the dispersing agent is preferably greater than or equal to 0.3 parts by mass and more preferably greater than or equal to 0.5 parts by mass, with respect to 100 parts by mass of all the monomers. In view of reducing the amount of mixture in hydrophilic polymer particles, the amount of the dispersing agent is preferably less than or equal to 20 parts by mass, more preferably less than or equal to 10 parts by mass, much more preferably less than or equal to 5 parts by mass, and yet more preferably less than or equal to 2 parts by mass, with respect to 100 parts by mass of all the monomers.

(3) Other Arbitrary Components

The oil-phase component may include other components that do not affect step 1: dispersion adjustment step and step 3: polymerization step below.

2. Aqueous-Phase Component

The aqueous-phase component is an aqueous solution including hydrophilic monomers, the polymerization initiator, and water.

(1) Hydrophilic Monomers

Examples of the hydrophilic monomers include: vinyl monomers and/or a salt thereof including cationic groups such as amino groups, ammonium groups, pyridyl groups, and imino groups (hereinafter referred to as "cationic monomers"); vinyl monomers including hydrophilic nonionic groups such as hydroxy groups, amide groups, ester groups, and ether groups (hereinafter referred to as "nonionic monomer"); vinyl monomers and/or a salt thereof including anionic groups such as carboxy groups, sulfonic groups, and phosphate groups (hereinafter referred to as "anionic monomers"); and vinyl monomers including hydrophilic amphoteric ionic groups and having betaine structures (hereinafter referred to as "amphoteric monomers"). Examples of the hydrophilic monomers also include crosslinkable vinyl monomers including at least two reactive unsaturated groups in a molecule (hereinafter referred to as "crosslinkable monomers").

In view of enhancing function and feeling, at least one of cationic monomers or nonionic monomers are preferably used as a constituent of the hydrophilic monomers. In view of affinity to the solvent, the amount of cationic monomers and/or nonionic monomers is preferably greater than or equal to 70 mass %, more preferably greater than or equal to 80 mass %, much more preferably greater than or equal to 95 mass %, and yet more preferably 100 mass %, with respect to the total amount of monomers except crosslinkable monomers.

In view of enhancing the viscosity of the aqueous solution obtained by dissolving hydrophilic polymer particles in water, crosslinkable monomers is preferably used as a constituent of the hydrophilic monomers. The amount of crosslinkable monomers is preferably greater than or equal to 0.005 parts by mass and more preferably greater than or equal to 0.01 part by mass, with respect to 100 parts by mass of monomers except the crosslinkable monomers. In view of reducing the viscosity of the aqueous solution obtained by dissolving hydrophilic polymer particles in water and the time of the dissolution of the hydrophilic polymer particles, the amount of crosslinkable monomers is preferably less than or equal to 5 parts by mass, more preferably less than or equal to 1 parts by mass, much more preferably less than or equal to 0.1 mass %, and yet more preferably 0.05 parts by mass, with respect to 100 parts by mass of monomers except the crosslinkable monomers.

(1-1) Cationic Monomers

In view of stability of physical properties of hydrophilic polymer particles to be obtained, the cationic monomers are preferably monomers including amino groups or a quaternary ammonium salt, and more preferably monomers including a quaternary ammonium salt. Examples of the monomers including a quaternary ammonium salt include (meta)acrylate including a quaternary ammonium salt group having a total carbon number of 2 to 44, (meta)acrylamide including a quaternary ammonium salt group having a total carbon number of 2 to 44, styrene including a quaternary ammonium salt group having a total carbon number of 2 to 44, N-vinyl heterocyclic compounds such as vinyl pyridine, alkylvinyl ether including a quaternary ammonium salt group having a total carbon number of 2 to 44, and vinyl monomers having a diallyl quaternary ammonium salt structure.

In view of stability of physical properties of hydrophilic polymer particles to be obtained, among the above-listed monomers, examples of preferred quaternary ammonium salt group-containing monomers include quaternary ammonium salt group-including monomers obtained by quaternizing dimethylaminoethyl(meta)acrylate, diethylaminoethyl(meta)acrylate, dimethylaminopropyl(meta)acrylamide, or diethylaminopropyl(meta)acrylamide, preferably dimethylaminoethyl(meta)acrylate, with diethyl sulfate, for example.

(1-2) Nonionic Monomers

Examples of nonionic monomers include vinyl alcohol, (meta)acrylate including a hydroxy alkyl group having a carbon number of 1 to 8, (meta)acrylamide including a hydroxy alkyl group having a carbon number of 1 to 8, (meta)acrylate of polyhydric alcohol, (meta)acrylamide, alkyl(meta)acrylamide having a carbon number of 1 to 8, dialkyl(meta)acrylamide having a total carbon number of 2 to 8, diacetone(meta)acrylamide, N-vinyl cyclic amide, (meta)acrylate including an alkyl group having a carbon number of 1 to 8, and (meta)acrylamide including a cyclic amide group. In view of reactivity of monomers, among the above-listed substances, alkyl(meta)acrylamide having a carbon number of 1 to 8 and dialkyl(meta)acrylamide having a total carbon number of 2 to 8 are preferable, and dialkyl(meta)acrylamide having a total carbon number of 2 to 8 is more preferable.

Examples of preferred (meta)acrylamide-based monomers include dialkyl(meta)acrylamide having a total carbon number of 2 to 8 such as N,N-dimethyl(meta)acrylamide and N,N-diethyl(meta)acrylamide. Between these substances, N,N-dimethyl(meta)acrylamide is preferable.

(1-3) Cross-Linkage Monomers

Cross-linkage monomers include at least two reactive unsaturated group in a molecule. Examples of the crosslinkable monomers include (meta)acrylate of polyhydric alcohol, acrylamide, divinyl compounds, polyallyl compounds, and (meta)acrylate of unsaturated alcohol. In view of reactivity of monomers, among these substances, ethylene glycol di(meta)acrylate and polyethylene glycol di(meta)acrylate are preferable, polyethylene glycol di(meta)acrylate is more preferable, and polyethylene glycol dimethacrylate is much more preferable.

(1-4) Anionic Monomers

Examples of the anionic monomers include carboxylic acid monomers including polymerizable unsaturated groups, acid anhydride of carboxylic acid monomers including polymerizable unsaturated groups, sulfonic acid monomers including polymerizable unsaturated groups, and phosphoric acid monomers including polymerizable unsaturated groups. Among these monomers, carboxylic acid monomers including polymerizable unsaturated groups, acid anhydride of carboxylic acid monomers including polymerizable unsaturated groups, and sulfonic acid monomers including polymerizable unsaturated groups are preferable.

The anionic groups may be neutralize at an arbitrary degree of neutralization with a basic substance. In this case, examples of cations in a salt in produced hydrophilic polymer particles include: ammonium ions; trialkyl ammonium ions having a total carbon number of alkyl group of 3 to 54 such as trimethylammonium ions and triethylammonium ions; hydroxy alkylammonium ions having a carbon number of 2 to 4; dihydroxy alkylammonium ions having a total carbon number of 4 to 8; trihydroxy alkylammonium ions having a total carbon number of 6 to 12; alkali metal ions; and alkaline-earth metal ions. These neutralizations may be performed with monomers or may be performed after production of hydrophilic polymer particles.

(1-5) Amphoteric Monomers

The amphoteric monomers are preferably at least one of monomers including polymerizable unsaturated groups and carboxy betaine groups or monomers including polymerizable unsaturated groups and sulfobetaine groups. Examples of the amphoteric monomers include N-methacroylethyl-N, N-dimethylammonium-N-methylcarboxybetaine, and 3-dimethyl(methacryloyloxyethyl)ammonium propanesulfonate.

(2) Polymerization Initiator

The polymerization initiator is preferably a radical polymerization initiator. In view of stable start of polymerization reaction, the polymerization initiator is preferably a polymerization initiator that is uniformly dissolved in the aqueous-phase component. Examples of the radical polymerization initiator include hydrogen peroxide, organic peroxide, a salt thereof, inorganic peroxide, a salt thereof, azobis-based compounds, and a redox-based polymerization initiator as a combination of an azobis-based compound and a reducer.

In view of increasing the conversion of polymerization reaction and reducing the amount of remaining monomers, the 10-hour half-life period temperature of the polymerization initiator is preferably greater than or equal to 10° C., more preferably greater than or equal to 30° C., and much more preferably greater than or equal to 50° C. In view of reducing the amount of the polymerization initiator remaining in the aqueous-phase component, the 10-hour half-life period temperature of the polymerization initiator is preferably less than or equal to 100° C., more preferably less than or equal to 80° C., and much more preferably less than or equal to 60° C. [Example] 56° C.

Specifically, examples of the polymerization initiator include: organic peroxide such as t-butyl peroxide, t-amyl peroxide, cumyl peroxide, benzoyl peroxide, 2,2'-azobisisobutyronitrile, 2,2'-azobis(2-amidinopropane)dihydrochloride, and 2,2'-azobis(2-(5-methyl-2-imidazoline-2-yl) dihydrochloride; persulfates such as sodium persulfate, potassium persulfate, and ammonium persulfate; hydrogen peroxide; and combinations of persulfate and tertiary amine such as triethylamine, triethanolamine, and diethylaniline. In view of the reaction rate, organic peroxide is preferable, 2,2'-azobisisobutyronitrile, 2,2'-azobis(2-amidinopropane) dihydrochloride, and 2,2'-azobis(2-(5-methyl-2-imidazoline-2-yl)dihydrochloride are more preferable, and 2,2'-azobis(2-amidinopropane)dihydrochloride is much more preferable. The polymerization initiator may be a single species or a mixture of a plurality of species.

In view of enhancing conversion of the polymerization reaction and reducing the amount of remaining monomers, the amount of the polymerization initiator is preferably greater than or equal to 0.01 part by mass, more preferably greater than or equal to 0.05 parts by mass, and much more preferably greater than or equal to 0.1 part by mass, with respect to 100 parts by mass of all the monomers. In view of reducing the content of a component derived from the polymerization initiator after the polymerization reaction, the amount of the polymerization initiator is preferably less than or equal to 5 parts by mass, more preferably less than or equal to 3 parts by mass, and much more preferably less than or equal to 1 part by mass, with respect to 100 parts by mass of all the monomers.

(3) Water

Examples of water include distilled water, deionized water, and tap water. In view of dispersing the aqueous-phase component in the oil-phase component, the amount of water is preferably 1 to 50% by volume (volume %), more preferably 5 to 40 volume %, and much more preferably 10 to 30 volume %, with respect to the total amount of the oil-phase component.

(4) Other Arbitrary Components

The aqueous-phase component may contain, as its constituents, the dispersing agent and the polymerization inhibitor described above, as necessary.

3. Preparation Method for Dispersion

Examples of methods for preparing a dispersion include a method for preparing a dispersion by supplying an aqueous-phase component including hydrophilic monomers, a polymerization initiator, and water to an oil-phase component including a hydrophobic solvent, a method for preparing a dispersion by supplying hydrophilic monomers and water from a supply port and a polymerization initiator from another supply port, at the same time to an oil-phase component including a hydrophobic solvent, and a method for preparing a dispersion by supplying hydrophilic monomers and water to an oil-phase component including a hydrophobic solvent and then supplying a polymerization initiator. Among these methods, in view of uniformly in mixing the dispersion, the method for preparing the dispersion by supplying the aqueous-phase component including hydrophilic monomers, the polymerization initiator, and water to the oil-phase component including the hydrophobic solvent is preferable.

Examples of a dispersion device for use in preparation of the dispersion include a stirring impeller in a reaction vessel, a high-pressure homogenizer including a driving unit, a line mixer, and a static mixer including no driving unit. Among these devices, the static mixer is preferable because of the ability of dispersion with low power and easiness of cleaning and maintenance of the mixer.

In the case of using the static mixer, the dispersion in which the aqueous-phase component is dispersed in the oil-phase component is preferably obtained by placing an external circulation line in the reaction vessel, allowing the static mixer to intervene in the external circulation line, and circulating the aqueous-phase component and the oil-phase component in the external circulation line so that the aqueous-phase component and the oil-phase component are distributed in the static mixer.

In this case, in view of enhancing dispersibility of the static mixer and reducing a pressure loss in the static mixer, the liquid flow rate of the aqueous-phase and oil-phase components or the dispersion to be distributed in the static mixer is preferably 0.1 to 1000 L/min, and more preferably 0.5 to 500 L/min. In view of controlling the start of the polymerization reaction, the temperature of the aqueous-phase and oil-phase components or the dispersion to be circulated in the external circulation line and distributed in the static mixer is less than or equal to the temperature at the start of polymerization of monomers, preferably less than or equal to 50° C., more preferably less than or equal to 40° C., and much more preferably less than or equal to 30° C., and in view of stability of the dispersion, the temperature is preferably greater than or equal to 0° C. and more preferably greater than or equal to 10° C.

In view of stability of the dispersion and effective removal of the hydrophobic solvent from hydrophilic polymer particles obtained by the polymerization reaction, the volume-average particle size in the aqueous-phase component included in the obtained dispersion is preferably greater than or equal to 0.1 µm, and is preferably less than or equal to 10 µm and more preferably less than or equal to 7 µm.

In view of productivity and effective removal of the hydrophobic solvent from the hydrophilic polymer particles obtained by the polymerization reaction, the coefficient of variation of the particle size in the aqueous-phase component is preferably greater than or equal to 1% and more preferably greater than or equal to 10%, and is preferably less than or equal to 60% and more preferably less than or equal to 55%.

(Step 2: Dissolved Oxygen Reduction Step)

In step 2, to control the start time of polymerization reaction, the concentration of oxygen dissolved in the dispersion obtained in step 1 is reduced.

With respect to the hydrophobic solvent, it is difficult to measure the absolute value of the dissolved oxygen concentration with an oximeter. Thus, the dissolved oxygen concentration of the dispersion in step 2 can be expressed as a relative value to the dissolved oxygen concentration before the reduction of the dissolved oxygen concentration, that is, the reduction ratio of the dissolved oxygen concentration of the dispersion. In view of control of start of the polymerization reaction, the reduction ratio of the dissolved oxygen concentration of the dispersion is preferably greater than or equal to 40%, more preferably greater than or equal to 60%, much more preferably greater than or equal to 70%, yet more preferably greater than or equal to 75%, and still more preferably greater than or equal to 80%, relative to the dissolved oxygen concentration at the start of the reduction of the dissolved oxygen concentration in step 2. In view of reducing the time necessary for step 2, the reduction ratio of the dissolved oxygen concentration of the dispersion is preferably less than or equal to 99% and more preferably less than or equal to 90%.

The dissolved oxygen concentration can be measured with a known method. Examples of the method for measuring the dissolved oxygen concentration include a method using a galvanic cell type oximeter and a method using a polarography type oximeter.

Examples of the method for reducing the dissolved oxygen concentration of the dispersion include a method of exhausting gas in a reaction vessel storing the dispersion prepared in step 1 to reduce the pressure of the vessel and then introducing an inert gas to the vessel so that the pressure of the vessel returns to the normal pressure, a method of directly introducing an inert gas into the dispersion, a method of distributing an inert gas in an upper space in the reaction vessel storing the dispersion, and a method of introducing an inert gas into the reaction vessel for pressurization, and exhausting gas from the reaction vessel so that the pressure of the vessel returns to the normal pressure.

Among these methods, in view of effective reduction of dissolved oxygen in the dispersion, the method of exhausting gas' in the reaction vessel to reduce the pressure of the vessel and then introducing the inert gas to the vessel so that the pressure of the vessel returns to the normal pressure is preferable. The inert gas herein refers to a gas that is inert to the polymerization reaction. Examples of the inert gas include nitrogen, argon, and helium. In view of industrial availability and ease of handling, nitrogen is preferable. The inert gas may be a single gas of a single species or a mixed gas including gases of a plurality of species. In view of the reduction efficiency of the dissolved oxygen concentration, the reduced pressure is preferably less than or equal to 40 kPa (absolute pressure) and more preferably less than or equal to 30 kPa (absolute pressure). In view of reducing a load of vacuum equipment, the reduced pressure is preferably greater than or equal to 1 kPa (absolute pressure), more preferably greater than or equal to 3 kPa (absolute pressure), much more preferably greater than or equal to 10 kPa (absolute pressure), and yet more preferably greater than or equal to 20 kPa (absolute pressure).

Operation of exhausting gas in the reaction vessel so that the pressure of the vessel returns to the normal pressure with the inert gas is preferably repeated in view of reducing the dissolved oxygen concentration. In view of reducing the dissolved oxygen concentration, the number of repetitions is preferably greater than or equal to 2 times (twice), more preferably greater than or equal to 3 times, and much more preferably greater than or equal to 4 times. In view of enhancing productivity, the time of repetitions is preferably less than or equal to 10 times, more preferably less than or equal to 8 times, and much more preferably less than or equal to 6 times.

In view of stability of the dispersion, the temperature of the dispersion in step 2 is preferably greater than or equal to 0° C., more preferably greater than or equal to 100° C., much more preferably greater than or equal to 20° C., and yet more preferably greater than or equal to 25° C. In view of control of start of the polymerization reaction, the temperature of the dispersion in step 2 is preferably less than or equal to 50° C., more preferably less than or equal to 40° C., much more preferably less than or equal to 35° C., and yet more preferably less than or equal to 30° C.

(Step 3: Polymerization Step)

In step 3, while the dispersion whose dissolved oxygen concentration has been reduced in step 2 is stirred in the reaction vessel and oxygen is supplied to the reaction vessel, the dispersion is heated in the reaction vessel so that the temperature of the dispersion increases, thereby polymerizing hydrophilic monomers in the aqueous phase. In this manner, hydrophilic polymer particles are dispersed in the oil-phase component in the resulting dispersion.

The point of time when heating for polymerization reaction starts in step 3 is after 0.1 hour or more and 3.5 hours or less from the start of reduction of the dissolved oxygen concentration of the dispersion in step 2. The point of time when heating for polymerization reaction starts in step 3 refers to the time when heating of the dispersion that is contained in the reaction vessel and has its oxygen concentration reduced in step 2 starts while oxygen is being supplied to the reaction vessel, i.e., the time when the rate of temperature increase reaches 1° C. or more per hour.

In view of effectively reducing dissolved oxygen in the dispersion in step 2, controlling start time of the polymerization reaction, and controlling viscosity of the aqueous solution in which obtained hydrophilic polymer particles are dissolved, the time from when reduction of the dissolved oxygen concentration of the dispersion starts in step 2 to when heating for polymerization reaction starts in step 3 is greater than or equal to 0.1 hour, preferably greater than or equal to 0.3 hours, more preferably greater than or equal to 0.5 hours, much more preferably greater than or equal to 0.7 hours, yet more preferably greater than or equal to 0.9 hours, and still more preferably greater than or equal to 1.0 hour. In view of controlling viscosity of the aqueous solution in which obtained hydrophilic polymer particles are dissolved, the time is less than or equal to 3.5 hours, preferably less than or equal to 3 hours, more preferably less than or equal to 2.5 hours, much more preferably less than or equal to 2.0 hours, yet more preferably less than or equal to 1.7 hours, and still more preferably less than or equal to 1.3 hours.

In view of the foregoing, the time is preferably in the range from 0.1 hour to 3.5 hours, inclusive, preferably in the range from 0.1 hour to 3 hours, inclusive, more preferably in the range from 0.1 hour to 2.5 hours, inclusive, much more preferably in the range from 0.1 hour to 2.0 hours, inclusive, yet more preferably in the range from 0.5 hours to 2.0 hours, inclusive, still more preferably in the range from 0.7 hours to 2.0 hours, inclusive, yet more preferably in the range from 0.9 hours to 1.7 hours, inclusive, and still more preferably in the range from 1.0 to 1.3 hours, inclusive.

In the method for producing hydrophilic polymer particles of this embodiment, the time from when reduction of the dissolved oxygen concentration of the dispersion in which the aqueous-phase component including hydrophilic monomers and the polymerization initiator are dispersed in the oil-phase component including the hydrophobic solvent starts to when heating of the dispersion starts is controlled so that the oxygen concentration in the reaction vessel before the reaction starts can be appropriately controlled and the reaction start time can be controlled to a constant time. Thus, hydrophilic polymer particles having a desired viscosity can be produced with stability.

In view of controlling the time when polymerization reaction starts and controlling viscosity of the aqueous solution in which obtained hydrophilic polymer particles are dissolved, the rate of temperature increase in the heating in step 3 is preferably less than or equal to 100° C. per hour, more preferably less than or equal to 80° C. per hour, much more preferably less than or equal to 70° C. per hour, yet more preferably less than or equal to 60° C. per hour, and still more preferably less than or equal to 50° C. per hour. In view of reducing the time necessary for temperature increase, controlling time when polymerization reaction starts, and controlling viscosity of the aqueous solution in which obtained hydrophilic polymer particles are dissolved, the rate of temperature increase is preferably greater than or equal to 1° C. per hour, more preferably greater than or equal to 5° C. per hour, much more preferably greater than or equal to 10° C. per hour, yet more preferably greater than or equal to 20° C. per hour, still more preferably greater than or equal to 35° C. per hour, and yet more preferably 40° C. per hour.

In view of controlling viscosity of the aqueous solution in which obtained hydrophilic polymer particles are dissolved, the amount of oxygen supplied to the dispersion in step 3 is greater than or equal to 0.02 volume % per hour (hereinafter referred to as %/h), preferably greater than or equal to 0.05 volume %/h, more preferably greater than or equal to 0.10 volume %/h, much more preferably greater than or equal to 0.20 volume %/h, and yet more preferably greater than or equal to 0.30 volume %/h, and is less than or equal to 0.9 volume %/h, preferably less than or equal to 0.8 volume %/h, more preferably less than or equal to 0.7 volume %/h, much more preferably less than or equal to 0.6 volume %/h, yet more preferably less than or equal to 0.5 volume %/h, still more preferably less than or equal to 0.45 volume %/h, and even more preferably less than or equal to 0.40 volume %/h, with respect to the volume of the dispersion obtained in step 2 under standard conditions (25° C., 101.3 kPa (absolute pressure)).

In view of the foregoing, the amount of oxygen supplied to the dispersion in step 3 is in the range from 0.02 volume %/h to 0.9 volume %/h, inclusive, preferably in the range from 0.05 volume %/h to 0.8 volume %/h, inclusive, more preferably in the range from 0.10 volume %/h to 0.8 volume %/h, inclusive, much more preferably in the range from 0.10 volume %/h to 0.5 volume %/h, inclusive, yet more preferably in the range from 0.10 volume %/h to 0.45 volume %/h, inclusive, still more preferably in the range from 0.30 volume %/h to 0.45 volume %/h, inclusive, and even more preferably in the range from 0.30 volume %/h to 0.40 volume %/h, inclusive, with respect to the volume of the dispersion obtained in step 2 under standard conditions (25° C., 101.3 kPa (absolute pressure)).

The method for supplying oxygen to the dispersion in step 3 may be, but is not limited to, oxygen supply from an oxygen source such as a compressor, a gas cylinder, or a gas storage tank, and oxygen supply caused by leakage due to a pressure difference between the reaction vessel and the outside of the reaction vessel when the inner pressure of the reaction vessel is reduced. Oxygen may be supplied to an inner space of the reaction vessel or into the liquid. In view of enhancing the rate of oxygen dissolution in the dispersion, oxygen is preferably supplied into the liquid.

In view of operability, the amount of oxygen supplied to the dispersion in step 3 is preferably adjusted by adjusting the opening degree of an oxygen introduction valve, adjusting the degree of pressure reduction of the reaction vessel, or adjusting air tightness of the reaction vessel, for example.

In the case of using an oxygen-containing gas for the supply of oxygen to the dispersion, in view of enhancing the rate of oxygen dissolution to the dispersion, the oxygen content in the oxygen-containing gas is preferably greater than or equal to 1 volume % and more preferably greater than or equal to 5 volume %. In view of ease of handling of the oxygen-containing gas, the oxygen content is preferably less than or equal to 50 volume %, and more preferably less than or equal to 40 volume %. Examples of the oxygen-containing gas include air.

In view of performing the polymerization reaction at a constant temperature with reflux of the hydrophobic solvent in the reaction, the pressure in the reaction vessel in step 3 is preferably less than or equal to 80 kPa (absolute pressure) and more preferably less than or equal to 60 kPa (absolute pressure). In view of reducing the load of vacuum equipment, the pressure is preferably greater than or equal to 1 kPa (absolute pressure), more preferably greater than or equal to 5 kPa (absolute pressure), much more preferably greater than or equal to 20 kPa (absolute pressure), and yet more preferably greater than or equal to 40 kPa (absolute pressure).

In view of enhancing the reaction rate, the reaction temperature in step 3, i.e., the temperature of the dispersion, is preferably greater than or equal to 40° C., more preferably greater than or equal to 45° C., and much more preferably greater than or equal to 50° C. In view of controlling the polymerization reaction, the reaction temperature is preferably less than or equal to 80° C., more preferably less than or equal to 75° C., much more preferably less than or equal to 70° C., and yet more preferably less than or equal to 60° C.

In view of enhancing productivity, in the dispersion in which the hydrophilic polymer particles obtained in step 3 are dispersed in the oil-phase component, the content of the hydrophilic polymer particles ((mass of hydrophilic polymer particles/(mass of hydrophilic polymer particles+mass of oil-phase component))×100) is preferably greater than or equal to 8 mass % and more preferably greater than or equal to 10 mass %, and in view of enhancing stability of the dispersion, the content is preferably less than or equal to 70 mass %, more preferably less than or equal to 50 mass %, much more preferably less than or equal to 30 mass %, and yet more preferably less than or equal to 20 mass %.

In view of productivity of hydrophilic polymer particles, the volume-average particle size of the hydrophilic polymer particles included in the dispersion obtained in step 3 is preferably greater than or equal to 0.1 µm, and in view of effective removal of the hydrophobic solvent from the hydrophilic polymer particles, the volume-average particle size is preferably less than or equal to 10 µm and more preferably less than or equal to 7 µm. In view of effective removal of the hydrophobic solvent from the hydrophilic polymer particles, the coefficient of variation of particle size of the hydrophilic polymer particles is preferably less than or equal to 60% and more preferably less than or equal to 55%. The volume-average particle size and coefficient of variation of particle size of the hydrophilic polymer particles can be obtained with a laser diffraction/scattering particle size distribution analyzer.

(Step 4: Dehydration Step)

The production method of this embodiment can include step 4, which is performed after step 3 and in which a dispersion of hydrophilic polymer particles having a water content reduced by dehydrating the dispersion obtained in step 3 is obtained.

Specifically, for example, the temperature of the dispersion of the hydrophilic polymer particles obtained by step 3 is increased in the reaction vessel so that water and the hydrophobic solvent are azeotroped, and the generated vapor is condensed by a condenser and is allowed to stand so that the vapor is separated into water and the hydrophobic solvent. Only the separated hydrophobic solvent is refluxed in the reaction vessel, whereas only water is caused to evaporate to be removed.

In step 4, in view of enhancing productivity, the temperature in the vessel is preferably greater than or equal to 60° C. and more preferably greater than or equal to 90° C., and in view of cost efficiency, the temperature is preferably less than or equal to 100° C. and more preferably less than or equal to 95° C. In view of reducing the water content, the dehydration time is preferably greater than or equal to 0.5 hours and more preferably greater than or equal to one hour, and in view of cost efficiency, the dehydration time is preferably less than or equal to 50 hours and more preferably less than or equal to 10 hours. The internal pressure of the vessel is reduced to, for example, 10 to 100 kPa (absolute pressure), as necessary.

In view of enhancing productivity, the content of hydrophilic polymer particles in the dispersion after the dehydration is preferably greater than or equal to 5 mass %, more preferably greater than or equal to 8 mass %, and much more preferably greater than or equal to 10 mass %. In view of reducing sedimentation of the hydrophilic polymer particles in the dispersion, the content is preferably less than or equal to 70 mass %, more preferably 50 mass %, much more preferably less than or equal to 30 mass %, and yet more preferably less than or equal to 20 mass %.

In view of productivity of hydrophilic polymer particles, the volume-average particle size of the hydrophilic polymer particles after the dehydration is preferably greater than or equal to 0.1 µm. In view of efficient removal of the hydrophobic solvent from the hydrophilic polymer particles, the volume-average particle size is preferably less than or equal to 10 µm and more preferably less than or equal to 7 µm. In view of efficient removal of the hydrophobic solvent from the hydrophilic polymer particles, the coefficient of variation of the hydrophilic polymer particles after dehydration is preferably less than or equal to 60% and more preferably less than or equal to 55%.

(Step 5: Solvent Substitution Step)

The production method of this embodiment can include step 5, which is performed after step 4 and in which a dispersion of hydrophilic polymer particles where the hydrophobic solvent of the dispersion obtained by dehydration in step 4 is substituted by a substitution solvent is obtained.

Specifically, for example, the substitution solvent is added to the dispersion obtained by dehydration in step 4, and then the temperature of the dispersion is increased in the reaction vessel so that the hydrophobic solvent is caused to evaporate to be removed.

In step 5, in view of enhancing productivity, the temperature in the vessel is preferably greater than or equal to 60° C. and more preferably greater than or equal to 70° C., and in view of cost efficiency, the temperature is preferably less than or equal to 100° C. and more preferably less than or equal to 90° C. In view of evaporation of the hydrophobic solvent, the evaporation time is preferably greater than or equal to 0.5 hours, more preferably greater than or equal to 10 hours, and much more preferably greater than or equal to 15 hours, and in view of cost efficiency, the evaporation time is preferably less than or equal to 50 hours, more preferably less than or equal to 40 hours, and much more preferably less than or equal to 30 hours. In view of enhancing productivity, the internal pressure of the vessel is preferably less than or equal to 100 kPa (absolute pressure) and more preferably less than or equal to 50 kPa (absolute pressure), and in view of cost efficiency, the internal pressure is preferably greater than or equal to 10 kPa (absolute pressure) and more preferably greater than or equal to 20 kPa (absolute pressure).

Examples of the substitution solvent include polyhydric alcohol, surfactants, and oils and fats. In view of preventing agglomeration of hydrophilic particles, the substitution solvent is preferably a surfactant. The substitution solvent may be a single species or a mixture of a plurality of species.

Examples of the surfactant include anionic surfactants such as polyoxyethylene alkyl ether sulfate, and nonionic surfactants such as polyoxyethylene alkyl ether and glycerin fatty acid ester. In view of preventing agglomeration of hydrophilic particles, the surfactant is preferably polyoxyethylene alkyl ether.

In view of enhancing stability in storage, the melting point of the substitution solvent is preferably greater than or equal to 10° C. and more preferably greater than or equal to 20° C. In view of preventing evaporation of the substitution solvent in the solvent substitution step, the boiling point of the substitution solvent under normal pressure is preferably greater than or equal to 101° C. and more preferably greater than or equal to 110° C.

In view of preventing agglomeration of hydrophilic polymer particles, the content of the substitution solvent in the resulting dispersion obtained by the substitution of the solvent in step 5 ((mass of substitution solvent/(mass of hydrophilic polymer particles+mass of substitution solvent))×100) is preferably greater than or equal to 10 mass %, more preferably greater than or equal to 20 mass %, much more preferably greater than or equal to 40 mass %, and yet more preferably greater than or equal to 50 mass %, and in view of enhancing productivity, the content is preferably less than or equal to 90 mass %, more preferably less than or equal to 80 mass %, and much more preferably less than or equal to 70 mass %.

In view of preventing agglomeration of hydrophilic polymer particles, the amount of the substitution solvent added relative to the total mass amount of monomers used for polymerization of the hydrophilic polymer particles is preferably greater than or equal to 0.3 kg of the substitution solvent per kg of total monomers, more preferably greater than or equal to 0.5 kg of the substitution solvent per kg of total monomers, much more preferably greater than or equal to 0.8 kg of the substitution solvent per kg of total monomers, and yet more preferably greater than or equal to 1.0 kg of substitution solvent per kg of total monomers. In view of enhancing productivity, the amount of the substitution solvent is preferably less than or equal to 10 kg of the substitution solvent per kg of total monomers, more preferably less than or equal to 8 kg of the substitution solvent per kg of total monomers, much more preferably less than or equal to 5 kg of the substitution solvent per kg of total monomers, and yet more preferably less than or equal to 2 kg of the substitution solvent per kg of total monomers.

In view of enhancing productivity, the content of hydrophilic polymer particles in the resulting dispersion obtained by the substitution of the solvent in step 5 ((mass of hydrophilic polymer particles/(mass of hydrophilic polymer particles+mass of substitution solvent))×100) is preferably greater than or equal to 10 mass %, more preferably greater than or equal to 20 weight %, and much more preferably greater than or equal to 30 mass %. In view of preventing agglomeration of hydrophilic polymer particles, the content of hydrophilic polymer particles is preferably less than or equal to 90 weight %, more preferably less than or equal to 80 weight %, much more preferably less than or equal to 60 mass %, and yet more preferably less than or equal to 50 mass %. The content of the hydrophilic polymer particles can be controlled by adjusting the amount of the substitution solvent.

The volume-average particle size and coefficient of variation of the hydrophilic polymer particles included in the dispersion obtained in step 5 are substantially the same as those of the hydrophilic polymer particles obtained in step 4. The volume-average particle size of the hydrophilic polymer particles is preferably less than or equal to 10 μm, more preferably less than or equal to 7 μm, and is preferably greater than or equal to 0.1 μm. The coefficient of variation of the hydrophilic polymer particles is preferably less than or equal to 60% and more preferably less than or equal to 55%.

In view of improving feeling of cosmetics or cleansing agents including the hydrophilic polymer particles, the viscosity at 30° C. of an aqueous solution prepared by dissolving the dispersion obtained in step 5 in water with a concentration of the hydrophilic polymer particles of 1.0 mass % is preferably greater than or equal to 1500 mPa·s, more preferably greater than or equal to 1700 mPa·s, much more preferably greater than or equal to 2000 mPa·s, yet more preferably greater than or equal to 2100 mPa·s, and still more preferably greater than or equal to 2300 mPa·s, and is preferably less than or equal to 4000 mPa·s, more preferably less than or equal to 3300 mPa·s, much more preferably less than or equal to 2800 mPa·s, and yet more preferably less than or equal to 2600 mPa·s. As will be described in Examples later, the viscosity at 30° C. of the aqueous solution can be measured with a B-type viscometer.

(Filtering and Drying Step)

Powder of hydrophilic polymer particles may be obtained by filtering hydrophilic polymer particles with a known method from the dispersion obtained in any one of steps 3, 4, and 5 and drying the obtained solid content as necessary.

In this case, in view of reducing agglomeration of particles, it is preferable to filter and dry the solid content of the hydrophilic polymer particles from the dispersion obtained in step 4 or 5.

The hydrophilic polymer particles obtained by the production method of this embodiment can be used for additives of cosmetics and/or cleansing agents, carriers of various chemical substances, and surface modifiers for recording paper.

With respect to the foregoing embodiment, a method for producing hydrophilic polymer particles will now be described.

<1> A method for producing hydrophilic polymer particles includes:

step 1 of preparing a dispersion in which an aqueous-phase component including hydrophilic monomers and a polymerization initiator is dispersed in an oil-phase component including a hydrophobic solvent having a solubility of 1 mass % or less in water at 25° C.;

step 2 of reducing a dissolved oxygen concentration of the dispersion prepared in step 1; and step 3 of polymerizing the hydrophilic monomers in the aqueous phase by supplying oxygen to a reaction vessel and, while oxygen is being supplied, heating the dispersion whose dissolved oxygen concentration was reduced in step 2 in the reaction vessel so that a temperature of the dispersion increases, wherein a time from a start of reduction of the dissolved oxygen concentration of the dispersion in step 2 to a start of heating of the dispersion in step 3 is greater than or equal to 0.1 hour and less than or equal to 3.5 hours, and an amount of oxygen supplied to the reaction vessel in step 3 is greater than or equal to 0.02 volume % per hour and less than or equal to 0.9 volume % per hour with respect to a volume of the dispersion, under standard conditions of a temperature of 25° C. and an absolute pressure of 101.3 kPa.

<2> In the method for producing hydrophilic polymer particles in <1>, the time from the start of reduction of the dissolved oxygen concentration of the dispersion in step 2 to the start of heating of the dispersion in step 3 is greater than or equal to 0.1 hour, and preferably greater than or equal to 0.3 hours, more preferably greater than or equal to 0.5 hours, much more preferably greater than or equal to 0.7 hours, yet more preferably greater than or equal to 0.9 hours, and still more preferably greater than or equal to 1.0 hour, and is less than or equal to 3.5 hours, preferably less than or equal to 3 hours, more preferably less than or equal to 2.5 hours, much more preferably less than or equal to 2.0 hours, yet more preferably less than or equal to 1.7 hours, and still more preferably less than or equal to 1.3 hours.

<3> In the method for producing hydrophilic polymer particles in <1>, the time from the start of reduction of the dissolved oxygen concentration of the dispersion in step 2 to the start of heating of the dispersion in step 3 is greater than or equal to 0.1 hour and less than or equal to 3.5 hours, preferably greater than or equal to 0.1 hour and less than or equal to 3 hours, more preferably greater than or equal to 0.1 hour and less than or equal to 2.5 hours, much more preferably greater than or equal to 0.1 hour and less than or equal to 2.0 hours, yet more preferably greater than or equal to 0.5 hours and less than or equal to 2.0 hours, still more preferably greater than or equal to 0.7 hours and less than or equal to 2.0 hours, even more preferably greater than or equal to 0.9 hours and less than or equal to 1.7 hours, and still more preferably greater than or equal to 1.0 hour and less than or equal to 1.3 hours.

<4> In the method for producing hydrophilic polymer particles of any one of <1> to <3>, the amount of oxygen supplied to the reaction vessel in step 3 is greater than or equal to 0.02 volume %/h per hour, preferably greater than or equal to 0.05 volume %/h, more preferably greater than or equal to 0.10 volume %/h, much more preferably greater than or equal to 0.20 volume %/h, and yet more preferably greater than or equal to 0.30 volume %/h, and is less than or equal to 0.9 volume %/h, preferably less than or equal to 0.8 volume %/h, more preferably less than or equal to 0.7 volume %/h, much more preferably less than or equal to 0.6 volume %/h, yet more preferably less than or equal to 0.5 volume %/h, still more preferably less than or equal to 0.45 volume %/h, and even more preferably less than or equal to 0.40 volume %/h, with respect to the volume of the dispersion obtained in step 2 under standard conditions of a temperature of 25° C. and an absolute pressure of 101.3 kPa.

<5> In the method for producing hydrophilic polymer particles of any one of <1> to <3>, the amount of oxygen supplied to the reaction vessel in step 3 is greater than or equal to 0.02 volume %/h and less than or equal to 0.9 volume %/h, preferably greater than or equal to 0.05 volume %/h and less than or equal to 0.8 volume %/h, more preferably greater than or equal to 0.10 volume %/h and less than or equal to 0.8 volume %/h, much more preferably greater than or equal to 0.10 volume %/h and less than or equal to 0.5 volume %/h, yet more preferably greater than or equal to 0.10 volume %/h and less than or equal to 0.45 volume %/h, still more preferably greater than or equal to 0.30 volume %/h and less than or equal to 0.45 volume %/h, and even more preferably greater than or equal to 0.30 volume %/h and less than or equal to 0.40 volume %/h, with respect to the volume of the dispersion obtained in step 2 under standard conditions of a temperature of 25° C. and an absolute pressure of 101.3 kPa.

<6> In the method for producing hydrophilic polymer particles of any one of <1> to <5>, a method used in step 1 of preparing the dispersion is preferably a method for preparing the dispersion by supplying the aqueous-phase component including hydrophilic monomers, the polymerization initiator, and water to the oil-phase component including the hydrophobic solvent, a method for preparing the dispersion by simultaneously supplying hydrophilic monomers and water to the oil-phase component including the hydrophobic solvent through a supply port and supplying the polymerization initiator to the oil-phase component through another supply port, or a method for preparing the dispersion by supplying hydrophilic monomers and water to the oil-phase component including the hydrophobic solvent and then supplying the polymerization initiator to the oil-phase component including the hydrophobic solvent, and more preferably the step of preparing the dispersion by supplying the aqueous-phase component including hydrophilic monomers, the polymerization initiator, and water to the oil-phase component including the hydrophobic solvent.

<7> In the method for producing hydrophilic polymer of <6>, a dispersion device for use in preparing the dispersion in step 1 is preferably a high-pressure homogenizer, a line mixer, or a static mixer, and is more preferably the static mixer.

<8> In the method for producing hydrophilic polymer of <7>, in the case of using the static mixer as the dispersion device for use in preparing the dispersion in step 1, the temperature of the aqueous-phase component and the oil-phase component or the dispersion distributed in the static mixer is preferably less than or equal to 50° C., more preferably less than or equal to 40° C., and much more preferably less than or equal to 30° C., and is preferably greater than or equal to 0° C. and more preferably greater than or equal to 10° C.

<9> In method for producing hydrophilic polymer particles of any one of <1> to <8>, in step 2, with respect to the dissolved oxygen concentration of the dispersion at the start of reducing the dissolved oxygen concentration, the dissolved oxygen concentration of the dispersion is preferably reduced by greater than or equal to 40%, more preferably greater than or equal to 60%, much more preferably greater than or equal to 70%, yet more preferably greater than or equal to 75%, and still more preferably greater than or equal to 80%, and is preferably reduced by less than or equal to 99% and more preferably less than or equal to 90%.

<10> In the method for producing hydrophilic polymer particles of any one of <1> to <9>, the step of reducing the dissolved oxygen concentration of the dispersion in step 2 is preferably the step of exhausting a gas in the reaction vessel storing the dispersion prepared in step 1 to reduce the pressure of the reaction vessel and then introducing an inert gas into the reaction vessel in order to return the pressure of the reaction vessel to a normal pressure, the step of directly introducing an inert gas into the dispersion, the step of distributing an inert gas in an upper space of the reaction vessel storing the dispersion, or the step of introducing an inert gas into the reaction vessel to increase the pressure of the reaction vessel and then exhausting the gas from the reaction vessel in order to return the pressure of the reaction vessel to a normal pressure, and is more preferably the step of exhausting a gas in the reaction vessel storing the dispersion prepared in step 1 to reduce the pressure of the reaction vessel and then introducing an inert gas into the reaction vessel in order to return the pressure of the reaction vessel to a normal pressure.

<11> In the method for producing hydrophilic polymer particles of <10>, in a case where the step of reducing the dissolved oxygen concentration of the dispersion in step 2 is the step of exhausting a gas in the reaction vessel storing the dispersion prepared in step 1 to reduce the pressure of the reaction vessel and then introducing an inert gas into the reaction vessel in order to return the pressure of the reaction vessel to a normal pressure, the inert gas to be introduced is preferably a nitrogen, argon, or helium, and is more preferably nitrogen.

<12> In the method for producing hydrophilic polymer particles of <10> or <11>, in a case where the step of reducing the dissolved oxygen concentration of the dispersion in step 2 is the step of exhausting a gas in the reaction vessel storing the dispersion prepared in step 1 to reduce the pressure of the reaction vessel and then introducing an inert gas into the reaction vessel in order to return the pressure of the reaction vessel to a normal pressure, the reduced pressure is preferably less than or equal to 40 kPa (absolute pressure) and more preferably less than or equal to 30 kPa (absolute pressure), and is preferably greater than or equal to 1 kPa (absolute pressure), more preferably greater than or equal to 3 kPa (absolute pressure), much more preferably greater than or equal to 10 kPa (absolute pressure), and yet more preferably greater than or equal to 20 kPa (absolute pressure).

<13> In the method for producing hydrophilic polymer particles of any one of <10> to <12>, in a case where the step of reducing the dissolved oxygen concentration of the dispersion in step 2 is the step of exhausting a gas in the reaction vessel storing the dispersion prepared in step 1 to reduce the pressure of the reaction vessel and then introducing an inert gas into the reaction vessel in order to return the pressure of the reaction vessel to a normal pressure, the number of repetitions of operation of exhausting a gas in the reaction vessel to return the pressure to the normal pressure with the inert gas is preferably greater than or equal to 2 times (twice), more preferably greater than or equal to 3 times, and much more preferably greater than or equal to 4 times, and is preferably less than or equal to 10 times, more preferably less than or equal to 8 times, and much more preferably less than or equal to 6 times.

<14> In the method for producing hydrophilic polymer particles of any one of <1> to <13>, the temperature of the dispersion in step 2 is preferably greater than or equal to 0° C., more preferably greater than or equal to 10° C., much more preferably greater than or equal to 20° C., and still more preferably greater than or equal to 25° C., and is preferably less than or equal to 50° C., more preferably less than or equal to 40° C., much more preferably less than or equal to 35° C., and yet more preferably less than or equal to 30° C.

<15> In the method for producing hydrophilic polymer particles of any one of <1> to <14>, a rate of temperature increase of the dispersion in step 3 is preferably less than or equal to 100° C. per hour, more preferably less than or equal to 80° C. per hour, much more preferably less than or equal to 70° C. per hour, yet more preferably less than or equal to 60° C. per hour, and even more preferably less than or equal to 50° C. per hour, and is preferably greater than or equal to 1° C. per hour, more preferably greater than or equal to 5° C. per hour, much more preferably greater than or equal to 10° C. per hour, yet more preferably greater than or equal to 20° C. per hour, still more preferably greater than or equal to 35° C. per hour, and even more preferably greater than or equal to 40° C. per hour.

<16> In the method for producing hydrophilic polymer particles of any one of <1> to <15>, in step 3, oxygen is preferably supplied into a space of the reaction vessel or the solution in the reaction vessel, and is more preferably supplied into the solution in the reaction vessel.

<17> In the method for producing hydrophilic polymer particles of any one of <1> to <16>, an oxygen-containing gas is used for oxygen supply to the dispersion in step 3, and the oxygen content of the oxygen-containing gas is preferably greater than or equal to 1 volume % and more preferably greater than or equal to 5 volume %, an is preferably less than or equal to 50 volume % and more preferably less than or equal to 40 volume %.

<18> In the method for producing hydrophilic polymer particles of any one of <1> to <17>, air is used as an oxygen-containing gas in supplying oxygen to the dispersion in step 3.

<19> In the method for producing hydrophilic polymer particles of any one of <1> to <18>, the pressure in the reaction vessel in step 3 is preferably less than or equal to 80 kPa (absolute pressure) and more preferably less than or equal to 60 kPa (absolute pressure), and is preferably greater than or equal to 1 kPa (absolute pressure), more preferably greater than or equal to 5 kPa (absolute pressure), much more preferably greater than or equal to 20 kPa (absolute pressure), and yet more preferably greater than or equal to 40 kPa (absolute pressure).

<20> In the method for producing hydrophilic polymer particles of any one of <1> to <19>, the temperature of the dispersion in step 3 is preferably greater than or equal to 40° C., more preferably greater than or equal to 45° C., and much more preferably greater than or equal to 50° C., and is preferably less than or equal to 80° C., more preferably less <21> In the method for producing hydrophilic polymer particles of any one of <1> to <20>, the content of hydrophilic polymer particles in the dispersion in which the hydrophilic polymer particles obtained in step 3 are dispersed in the oil-phase component ((mass of hydrophilic polymer particles/(mass of hydrophilic polymer particles+mass of oil-phase component))×100) is preferably greater than or equal to 8 mass % and more preferably greater than or equal to 10 mass %, and is preferably less than or equal to 70 mass %, more preferably less than or equal to 50 mass %, much more preferably less than or equal to 30 mass %, and yet more preferably less than or equal to 20 mass %.

<22> In the method for producing hydrophilic polymer particles of any one of <1> to <21>, the hydrophobic solvent included in the oil-phase component in step 1 preferably includes at least one solvent selected from the group consisting of a hydrocarbon-based solvent, a halogenated hydrocarbon-based solvent, and an isoparaffin-based hydrocarbon-based solvent, and more preferably includes a hydrocarbon-based solvent, much more preferably at least one of hexane or cyclohexane, and yet more preferably includes cyclohexane.

<23> In the method for producing hydrophilic polymer particles of any one of <1> to <22>, the amount of the hydrophobic solvent in step 1 is preferably greater than or equal to one, more preferably greater than or equal to two, much more preferably greater than or equal to four, and yet more preferably greater than or equal to six, and is preferably less than or equal to twenty, more preferably less than or equal to seventeen, much more preferably less than or equal to fifteen, and yet more preferably less than or equal to ten times by mass as large as the total amount of monomers.

<24> In the method for producing hydrophilic polymer particles of any one of <1> to <23>, the hydrophilic monomer in step 1 includes at least one of cationic monomers or nonionic monomers.

<25> In the method for producing hydrophilic polymer particles of <24>, the amount of the cationic monomers or nonionic monomers and preferably greater than or equal to 70 mass %, more preferably greater than or equal to 80 mass %, much more preferably greater than or equal to 95 mass %, and yet more preferably greater than or equal to 100 mass %, with respect to the total amount of monomers except crosslinkable monomers.

<26> In the method for producing hydrophilic polymer particles of <24> or <25>, the cationic monomers are preferably monomers including amino groups or quaternary ammonium groups, more preferably include monomers including quaternary ammonium groups, much more preferably include at least one of (meta)acrylate including a quaternary ammonium salt group having a total carbon number of 2 to 44 or (meta)acrylamide including a quaternary ammonium salt group having a total carbon number of 2 to 44, yet more preferably include quaternary ammonium salt group-including monomers obtained by quaternizing, with, for example, diethyl sulfate, at least one material selected from the group consisting of dimethylaminoethyl (meta)acrylate, diethylaminoethyl(meta)acrylate, dimethylaminopropyl(meta)acrylamide, and diethylaminopropyl (meta)acrylamide, and still more preferably include quaternary ammonium salt group-including monomers obtained by quaternizing dimethylaminoethyl(meta)acrylate with, for example, diethyl sulfate.

<27> In the method for producing hydrophilic polymer particles of any one of <24> to <26>, the nonionic monomers preferably include at least one of alkyl(meta)acrylamide having a carbon number of 1 to 8 or dialkyl(meta)acrylamide having a total carbon number of 2 to 8, more preferably include dialkyl(meta)acrylamide having a total carbon number of 2 to 8, much more preferably include at least one of N,N-dimethyl(meta)acrylamide or N,N-diethyl(meta)acrylamide, and still more preferably include N,N-dimethyl(meta)acrylamide.

<28> In the method for producing hydrophilic polymer particles of any one of <1> to <27>, the hydrophilic monomers in step 1 include crosslinkable monomers.

<29> In the method for producing hydrophilic polymer particles of <28>, the amount of the crosslinkable monomers is preferably greater than or equal to 0.005 parts by mass and more preferably greater than or equal to 0.01 part by mass, and is preferably less than or equal to 5 parts by mass, more preferably less than or equal to 1 part by mass, much more preferably less than or equal to 0.1 part by mass, and yet more preferably less than or equal to 0.05 parts by mass, with respect to 100 parts by mass of monomers except the crosslinkable monomers.

<30> In the method for producing hydrophilic polymer particles of <28> or <29>, the crosslinkable monomers preferably include (meta)acrylate of polyhydric alcohol, more preferably include at least one of ethylene glycol di(meta)acrylate or polyethylene glycol di(meta)acrylate, much more preferably include polyethylene glycol di(meta)acrylate, and yet more preferably include polyethylene glycol dimethacrylate.

<31> In the method for producing hydrophilic polymer particles of any one of <1> to <30>, the polymerization initiator included in the aqueous-phase component in step 1 is a radical polymerization initiator.

<32> In the method for producing hydrophilic polymer particles of <31>, the radical polymerization initiator preferably includes at least one material selected from the group consisting of hydrogen peroxide, organic peroxide, a salt thereof, inorganic peroxide, a salt thereof, an azobis-based compound, and a redox-based polymerization initiator as a combination of an azobis-based compound and a reducer, more preferably includes organic peroxide, much more preferably includes at least one material selected from the group consisting of 2,2'-azobisisobutyronitrile, 2,2'-azobis (2-amidinopropane)dihydrochloride, and 2,2'-azobis(2-(5-methyl-2-imidazoline-2-yl)dihydrochloride, and yet more preferably includes 2,2'-azobis(2-amidinopropane)dihydrochloride.

<33> The method for producing hydrophilic polymer particles of <31> or <32>, the 10-hour half-life period temperature of the radical polymerization initiator is preferably greater than or equal to 10° C., more preferably greater than or equal to 20° C., and much more preferably greater than or equal to 30° C., and is preferably less than or equal to 100° C., more preferably less than or equal to 90° C., and much more preferably less than or equal to 80° C.

<34> In the method for producing hydrophilic polymer particles of any one of <1> to <33>, the amount of the polymerization initiator included in the aqueous-phase component in step 1 is preferably greater than or equal to 0.01 part by mass, more preferably greater than or equal to 0.05 parts by mass, much more preferably greater than or equal to 0.1 part by mass, and is preferably less than or equal to 5 parts by mass, much more preferably less than or equal to 3 parts by mass, and yet more preferably less than or equal to 1 part by mass, with respect to 100 parts by mass of total monomers.

<35> In the method for producing hydrophilic polymer particles of any one of <1> to <34>, the amount of water included in the aqueous-phase component in step 1 is preferably 1 to 50 volume %, more preferably 5 to 40 volume %, and much more preferably 10 to 30 volume %, with respect to the total amount of the oil-phase component.

<36> In the method for producing hydrophilic polymer particles of any one of <1> to <35>, the dispersion is prepared by using the oil-phase component including a dispersing agent in step 1.

<37> In the method for producing hydrophilic polymer particles of <36>, the dispersing agent included in the oil-phase component preferably includes at least one material selected from the group consisting of a nonionic surfactant, an anionic surfactant, a cationic surfactant, and an amphoteric surfactant, more preferably includes a nonionic surfactant, much more preferably includes a polyhydric alcohol-type surfactant, yet more preferably includes at least one of sorbitan stearate or sucrose stearate, and still more preferably includes sucrose stearate.

<38> In the method for producing hydrophilic polymer particles of <36> or <37>, the dispersing agent included in the oil-phase component is a surfactant having a hydrophilic-lipophilic balance of preferably 4 to 30, more preferably 5 to 20, and much more preferably 6 to 10.

<39> In the method for producing hydrophilic polymer particles of any one of <36> to <38>, the amount of the dispersing agent included in the oil-phase component is preferably greater than or equal to 0.3 parts by mass and more preferably greater than or equal to 0.5 parts by mass, and is preferably less than or equal to 20 parts by mass, more preferably less than or equal to 10 parts by mass, much more preferably less than or equal to 5 parts by mass, and yet more preferably less than or equal to 2 parts by mass, with respect to 100 parts by mass of total monomers.

<40> The method for producing hydrophilic polymer particles of any one of <1> to <39> further includes step 4 of reducing the content of water by dehydration the dispersion of the hydrophilic polymer particles obtained in step 3.

<41> In the method for producing hydrophilic polymer particles of <40>, step 4 is the step of increasing the temperature of the dispersion of the hydrophilic polymer particles obtained in step 3 in the reaction vessel so as to azeotrope water and the hydrophobic solvent, condensing the generated vapor in a condenser, then separating the vapor into water and the hydrophobic solvent, and evaporating and removing only the separated water from the vapor.

<42> In the method for producing hydrophilic polymer particles of <40> or <41>, the temperature in the vessel in step 4 is preferably greater than or equal to 60° C. and more preferably greater than or equal to 90° C., and is preferably less than or equal to 100° C. and more preferably less than or equal to 95° C.

<43> In the method for producing hydrophilic polymer particles of any one of <40> to <42>, the content of hydrophilic polymer particles in the dispersion after the dehydration in step 4 is preferably greater than or equal to 5 mass %, more preferably greater than or equal to 8 mass %, and much more preferably greater than or equal to 10 mass %, and is preferably less than or equal to 70 mass %, more preferably less than or equal to 50 mass %, much more preferably less than or equal to 30 mass %, and yet more preferably less than or equal to 20 mass %.

<44> The method for producing hydrophilic polymer particles of any one of <40> to <43> further includes step 5 of substituting, by a substitution solvent, the hydrophobic solvent included in the dispersion of the hydrophilic polymer particles dehydrated in step 4.

<45> In the method for producing hydrophilic polymer particles of <44>, the temperature in the vessel in step 5 is preferably greater than or equal to 60° C. and more preferably greater than or equal to 70° C., and is preferably less than or equal to 100° C. and more preferably less than or equal to 90° C.

<46> In the method for producing hydrophilic polymer particles of <44> or <45>, the internal pressure of the vessel in step 5 is preferably less than or equal to 100 kPa (absolute pressure) and more preferably greater than or equal to 50 kPa (absolute pressure), and is preferably greater than or equal to 10 kPa (absolute pressure) and more preferably greater than or equal to 20 kPa (absolute pressure).

<47> In the method for producing hydrophilic polymer particles of any one of <44> to <46>, the substitution solvent preferably includes at least one of a material selected from the group consisting of polyhydric alcohol, a surfactant, and oils and fats, more preferably includes a surfactant, much more preferably includes at least one of an anionic surfactant or a nonionic surfactant, yet more preferably includes a nonionic surfactant, still more preferably includes at least one of polyoxyethylene alkyl ether or glycerin fatty acid ester, and even more preferably includes polyoxyethylene alkyl ether <48> In the method for producing hydrophilic polymer particles of any one of <44> to <47>, the melting point of the substitution solvent is preferably greater than or equal to 10° C. and more preferably greater than or equal to 20° C.

<49> In the method for producing hydrophilic polymer particles of any one of <44> to <48>, the content of the substitution solvent in the resulting dispersion obtained by the solvent substitution in step 5 (mass of substitution solvent/(mass of hydrophilic polymer particles+mass of substitution solvent)×100) is preferably greater than or equal to 10 mass %, more preferably greater than or equal to 20 mass %, much more preferably greater than or equal to 40 mass %, and yet more preferably greater than or equal to 50 mass %, and is preferably less than or equal to 90 mass %, more preferably less than or equal to 80 mass %, and much more preferably less than or equal to 70 mass %.

<50> In the method for producing hydrophilic polymer particles of any one of <44> to <49>, the amount of the substitution solvent added to the total mass amount of monomers for use in polymerization of hydrophilic polymer particles in step 5 is preferably greater than or equal to 0.3 kg of the substitution solvent per kg of total monomers, more preferably greater than or equal to 0.5 kg of the substitution solvent per kg of total monomers, much more preferably greater than or equal to 0.8 kg of the substitution solvent per kg of total monomers, and yet more preferably greater than or equal to 1.0 kg of the substitution solvent per kg of total monomers, and is preferably less than or equal to 10 kg of the substitution solvent per kg of total monomers, more preferably less than or equal to 8 kg of the substitution solvent per kg of total monomers, much more preferably less than or equal to 5 kg of the substitution solvent per kg of total monomers, and yet more preferably less than or equal to 2 kg of the substitution solvent per kg of total monomers.

<51> In the method for producing hydrophilic polymer particles of any one of <44> to <50>, the content of hydrophilic polymer particles in the resulting dispersion obtained by the substitution solvent in step 5 ((mass of hydrophilic polymer particles/(mass of hydrophilic polymer particles+mass of substitution solvent))×100) is preferably greater than or equal to 10 mass %, more preferably greater than or equal to 20 mass %, and much more preferably greater than or equal to 30 mass %, and is preferably less than or equal to 90 mass %, more preferably less than or equal to 80 mass %, much more preferably less than or equal to 60 mass %, and yet more preferably less than or equal to 50 mass %.

<52> In the method for producing hydrophilic polymer particles of any one of <44> to <51>, the viscosity at 30° C. of an aqueous solution prepared by dissolving the dispersion obtained in step 5 in water so that the concentration of hydrophilic polymer particles is adjusted to 1.0 mass % is preferably greater than or equal to 1500 mPa·s, more preferably greater than or equal to 1700 mPa·s, much more preferably greater than or equal to 2000 mPa·s, yet more preferably greater than or equal to 2100 mPa·s, and still more preferably greater than or equal to 2300 mPa·s, and is preferably less than or equal to 4000 mPa·s, more preferably less than or equal to 3300 mPa·s, much more preferably less than or equal to 2800 mPa·s, and yet more preferably less than or equal to 2600 mPa·s.

EXAMPLES

Measurement Method

<Method for Measuring Viscosity of Hydrophilic Polymer Aqueous Solution>

Aqueous solutions having a hydrophilic polymer particle concentration of 1.0 mass % were obtained by adding deionized water to dispersions of hydrophilic polymer particles obtained in Examples 1 to 11 and Comparative Examples 1 to 5 below and stirring the resulting aqueous solution until the hydrophilic polymer particles were completely dissolved, and the viscosity of the aqueous solution at 30° C. was measured with a B-type viscometer (TVB-15, produced by TOKI SANGYO Co., LTD.).

<Method for Measuring Dissolved Oxygen Concentration>

In Examples 1 to 11 and Comparative Examples 1 to 5 below, at each time of before and after reduction of the dissolved oxygen in step 2, a dispersion was taken from a sampling port in the bottom of a reaction vessel, and the dissolved oxygen concentration of the dispersion was measured with a galvanic cell type oximeter UC-12-SOL (produced by Central Kagaku Corp.). Then, the percentage of the relative value of the dissolved oxygen concentration after reduction of dissolved oxygen with respect to the dissolved oxygen concentration before the reduction of dissolved oxygen was obtained, and was defined as a reduction ratio of the dissolved oxygen concentration.

[Production of Hydrophilic Polymer Particles]

Hydrophilic polymer particles of Examples 1 to 11 and Comparative Examples 1 to 5 below were produced. Tables 1 and 2 show the details and results of the production.

Example 1

In Example 1, steps 1 to 5 were performed as follows:

(Step 1: Dispersion Preparation Step)

A 100-L reaction vessel was supplied with 44.9 kg of cyclohexane and 51.2 g of a dispersing agent (sucrose stearate (HLB=7), S-770 produced by Mitsubishi-Kagaku Foods Corporation). A 30-L monomer vessel was supplied with 1.5 kg of a 90% aqueous solution containing diethyl sulfate quaternized salt of 2-(dimethylamino)ethyl methacrylate (produced by Kao Corporation), 3.8 kg of N,N-dimethylacrylamide (produced by Kohjin Co., Ltd.), 1.1 g of polyethylene glycol dimethacrylate (NK ester 14G produced by Shin Nakamura Chemical Co., Ltd., molecular weight: 736), 7.3 kg of deionized water, and 25.2 g of a polymerization initiator (2,2'-azobis(2-amidinopropane)dihydrochloride, V-50 produced by Wako Pure Chemical Industries, Ltd., 10-hour half-life period temperature: 56° C.).

Thereafter, while a mixture solution of cyclohexane and the dispersing agent was stirred in the reaction vessel, the aqueous-phase component including monomers and the polymerization initiator was supplied to the reaction vessel from the monomer vessel, and then the mixture was further stirred, thereby obtaining a solution mixture.

Subsequently, the solution mixture in the reaction vessel was heated to 27° C., and the solution mixture was caused to circulate in a circulation line in which a static mixer was interposed, thereby preparing a dispersion.

While the obtained dispersion was stirred in the reaction vessel, the temperature of the dispersion was adjusted to 27 to 28° C.

(Step 2: Dissolved Oxygen Reduction Step)

The pressure in the reaction vessel was reduced from the atmospheric pressure to 26.7 kPa (absolute pressure), and then a nitrogen gas was introduced into the reaction vessel so that the pressure returns to the atmospheric pressure. This so-called nitrogen substitution operation, i.e., dissolved oxygen concentration reducing operation, was performed five times in total. The reduction ratio of the dissolved oxygen concentration obtained by this operation was 83%. The time required for the nitrogen substitution operation was 1.4 hours.

(Step 3: Polymerization Step)

The internal pressure of the reaction vessel was set at 57 kPa (absolute pressure), and air (oxygen content: 21 volume %) was supplied as an oxygen-containing gas to the dispersion. The amount of this oxygen supply was controlled to be 0.60 volume %/h with respect to the volume of the dispersion in the reaction vessel under standard conditions (25° C., 101.3 kPa (absolute pressure)).

After 2.6 hours from the start of the nitrogen substitution operation in step 2, i.e., the start of reduction of the dissolved oxygen concentration, heating of the dispersion was started so that the temperature of the dispersion in the reaction vessel was increased to 54 to 57° C., and polymerization reaction was performed for 40 minutes in this temperature range, thereby obtaining a dispersion in which hydrophilic polymer particles were dispersed. The heating of the dispersion was started after 0.2 hours from the start of oxygen supply to the dispersion, where the rate of temperature increase of the dispersion was 50.8° C. per hour.

(Step 4: Dehydration Step)

After the polymerization reaction in step 3, the jacket temperature of the reaction vessel was set at 95° C., and cyclohexane and water were evaporated and removed from the reaction vessel, thus performing dehydration. A fraction was obtained by condensing the vapor in a condenser, separating the condensed vapor into water and cyclohexane while allowing the vapor to stand. During the dehydration, the separated cyclohexane was continuously refluxed in the reaction vessel, whereas only water was caused to evaporate be removed from the reaction vessel. The time required for the dehydration was 6.9 hours.

(Step 5: Solvent Substitution Step)

To the dispersion obtained in step 4, 6.5 kg of polyoxyethylene alkyl ether (Emulgen 116 produced by Kao Corporation, molecular weight: 891, melting point: 25° C.) was added, the jacket temperature was set at 80° C., and the internal pressure of the vessel was reduced to 26.7 kPa (absolute pressure), thereby evaporating and removing cyclohexane.

Then, a solution mixture of 1.3 kg of polyoxyethylene alkyl ether and 0.15 kg of deionized water was added to the dispersion, the jacket temperature was set at 80° C. again, and the internal pressure of the vessel was reduced to 40 kPa (absolute pressure), thereby performing second evaporation of cyclohexane. In this manner, a dispersion including 5.2 kg of hydrophilic polymer particles was obtained. The time required for the evaporation was 23.1 hours in total.

The viscosity at 30° C. of an aqueous solution prepared by dissolving the obtained dispersion in water with a concentration of hydrophilic polymer particles of 1.0 mass %, was 3470 mPa·s. A shampoo having a composition shown in Table 3 and prepared by using the dispersion including the obtained hydrophilic polymer particles, exhibited a sufficient degree of smoothness and light feeling at a rinse.

Example 2

In Example 2, the same operation as that of Example 1 was performed except that the oxygen supply amount in step 3 was 0.35 volume %/h and heating of the dispersion was started after 1.7 hours from the start of the nitrogen substitution operation in step 2. In step 2, the reduction ratio of the dissolved oxygen concentration was 89%, and the time required for the nitrogen substitution operation was 1.3 hours. In step 3, heating of the dispersion was started after 0.2 hours from the start of oxygen supply to the dispersion, and the rate of temperature increase of the dispersion was 46.9° C. per hour. In step 4, the time required for the dehydration was 5.8 hours. In step 5, the time required for the evaporation was 21.1 hours in total.

The viscosity at 30° C. of the aqueous solution prepared by dissolving the obtained dispersion in water and setting the concentration of hydrophilic polymer particles at 1.0 mass % was 2660 mPa·s.

Example 3

In Example 3, the same operation as that in Example 1 was performed except that the oxygen supply amount in step 3 was 0.35 volume %/h and heating of the dispersion was started after 1.0 hour from the start of the nitrogen substitution operation in step 2. In step 2, the reduction ratio of the dissolved oxygen concentration was 77%, and the time required for the nitrogen substitution operation was 0.9 hours. In step 3, heating of the dispersion was started after 0.1 hour from the start of oxygen supply to the dispersion, and the rate of temperature increase of the dispersion was 47.8° C. per hour. In step 4, the time required for the dehydration was 6.6 hours. In step 5, the time required for the evaporation was 20.7 hours in total.

The viscosity at 30° C. of the aqueous solution prepared by dissolving the obtained dispersion in water and setting the concentration of hydrophilic polymer particles at 1.0 mass % was 2500 mPa·s. A shampoo having a composition shown in Table 3 and prepared by using the dispersion including the obtained hydrophilic polymer particles, exhibited a high degree of smoothness and sustained smoothness at a rinse.

Example 4

In Example 4, the same operation as that of Example 1 was performed except that the nitrogen substitution operation in step 2 was performed three times, the oxygen supply amount in step 3 was 0.35 volume %/h, and heating of the dispersion was started after 0.9 hours from the start of the nitrogen substitution operation in step 2. The reduction ratio of the dissolved oxygen concentration in step 2 was 64%, and the time required for the nitrogen substitution operation was 0.7 hours. In step 3, heating of the dispersion was started after 0.2 hours from the start of oxygen supply to the dispersion, and the rate of temperature increase of the dispersion was 45.0° C. per hour. In step 4, the time required for the dehydration was 6.9 hours. In step 5, the time required for the evaporation was 24.2 hours in total.

The viscosity at 30° C. of the aqueous solution prepared by dissolving the obtained dispersion in water and setting the concentration of hydrophilic polymer particles at 1.0 mass % was 2180 mPa·s.

Example 5

In Example 5, the same operation as that in Example 1 was performed except that the oxygen supply amount in step 3 was 0.77 volume %/h and heating of the dispersion was started after 1.6 hours from the start of the nitrogen substitution operation in step 2. In step 2, the reduction ratio of the dissolved oxygen concentration was 82%, and the time required for the nitrogen substitution operation was 1.3 hours. In step 3, heating of the dispersion was started after 0.1 hour from the start of oxygen supply to the dispersion, and the rate of temperature increase of the dispersion was 43.4° C. per hour. In step 4, the time required for the dehydration was 6.7 hours. In step 5, the time required for the evaporation was 21.0 hours in total.

The viscosity at 30° C. of the aqueous solution prepared by dissolving the obtained dispersion in water and setting the concentration of hydrophilic polymer particles at 1.0 mass % was 1640 mPa·s. A shampoo having a composition shown in Table 3 and prepared by using the dispersion including the obtained hydrophilic polymer particles, exhibited a sufficient degree of smoothness and soft-thick feeling at a rinse.

Example 6

In Example 6, the same operation as that in Example 1 was performed except that the oxygen supply amount in step 3 was 0.25 volume %/h and heating of the dispersion was started after 1.1 hour from the start of the nitrogen substitution operation in step 2. In step 2, the reduction ratio of the dissolved oxygen concentration was 60%, and the time required for the nitrogen substitution operation was 0.9 hours. In step 3, heating of the dispersion was started after 0.2 hours from the start of oxygen supply to the dispersion, and the rate of temperature increase of the dispersion was 46.3° C. per hour. In step 4, the time required for the dehydration was 7.7 hours. In step 5, the time required for the evaporation was 21.8 hours in total.

The viscosity at 30° C. of the aqueous solution prepared by dissolving the obtained dispersion in water and setting the concentration of hydrophilic polymer particles at 1.0 mass % was 2760 mPa·s.

Example 7

In Example 7, steps 1 to 5 were performed as follows:
(Step 1: Dispersion Preparation step)
A 5-L reaction vessel was supplied with 2.2 kg of cyclohexane and 2.6 g of a dispersing agent (sucrose stearate (HLB=7)). In addition, a 1-L monomer vessel was supplied with 75 g of a 90% aqueous solution containing diethyl sulfate quaternized salt of 2-(dimethylamino)ethyl methacrylate, 190 g of N,N-dimethylacrylamide, 0.06 g of polyethylene glycol dimethacrylate, 365 g of deionized water, 1.3 g of a polymerization initiator (2,2'-azobis(2-amidinopropane)dihydrochloride).

Next, while cyclohexane and the dispersing agent were stirred in the reaction vessel, the aqueous-phase component including monomers and the polymerization initiator was supplied to the reaction vessel from the monomer vessel, and then the mixture was further stirred, thereby obtaining a solution mixture.

Subsequently, the solution mixture in the reaction vessel was heated to 36° C., and was further mixed at 9000 rpm for 5 minutes with a homomixer (T.K. ROBO MICS produced by Tokushu Kika Kogyo Co., Ltd.), thereby preparing a dispersion.

While the obtained dispersion was stirred in the reaction vessel, the temperature of the dispersion was adjusted to 36 to 37° C.

(Step 2: Dissolved Oxygen Reduction Step)

The pressure in the reaction vessel was reduced from the atmospheric pressure to 26.7 kPa (absolute pressure), and then a nitrogen gas was introduced into the reaction vessel so that the pressure returns to the atmospheric pressure. This so-called nitrogen substitution operation was performed five times in total. The reduction ratio of the dissolved oxygen concentration obtained by this operation was 61%. The time required for the nitrogen substitution operation was 0.2 hours.

(Step 3: Polymerization Step)

The internal pressure of the reaction vessel was set at 57 kPa (absolute pressure), and air (oxygen content: 21 volume %) was supplied as an oxygen-containing gas to the dispersion. The amount of this oxygen supply was controlled to be 0.28 volume %/h with respect to the volume of the dispersion in the reaction vessel under standard conditions (25° C., 101.3 kPa (absolute pressure)).

After 0.3 hours from the start of the nitrogen substitution operation in step 2, heating of the dispersion was started so that the temperature of the dispersion in the reaction vessel was increased to 54 to 57° C., and polymerization reaction was performed for 40 minutes in this temperature range, thereby obtaining a dispersion in which hydrophilic polymer particles were dispersed. The heating of the dispersion was started after 0.1 hour from the start of oxygen supply to the dispersion, where the rate of temperature increase of the dispersion was 15.3° C. per hour.

(Step 4: Dehydration Step)

After the polymerization reaction in step 3, the jacket temperature of the reaction vessel was set at 95° C., and cyclohexane and water were evaporated and removed from the reaction vessel, thus performing dehydration. A fraction was obtained by condensing the vapor in a condenser, separating the condensed vapor into water and cyclohexane while allowing the vapor to stand. During the dehydration, the separated cyclohexane was continuously refluxed in the reaction vessel, whereas only water was caused to evaporate to be removed from the reaction vessel. The time required for the dehydration was 4.9 hours.

(Step 5: Solvent Substitution Step)

To the dispersion obtained in step 4, 325 g of polyoxyethylene alkyl ether was added, the jacket temperature was set at 80° C., and the internal pressure of the vessel was reduced to 26.7 kPa (absolute pressure), thereby evaporating and removing cyclohexane.

Then, a solution mixture of 65 g of polyoxyethylene alkyl ether and 7.5 g of deionized water was added to the dispersion, the jacket temperature was set at 80° C. again, and the internal pressure of the vessel was reduced to 40 kPa (absolute pressure), thereby performing second evaporation of cyclohexane. In this manner, a dispersion including 259 g of hydrophilic polymer particles was obtained. The time required for the evaporation was 17.7 hours in total.

The viscosity at 30° C. of the aqueous solution prepared by dissolving the obtained dispersion in water and setting the concentration of hydrophilic polymer particles at 1.0 mass % was 1990 mPa·s.

Example 8

In Example 8, the same operation as that of Example 7 was performed except that the temperature of the dispersion in step 2 was adjusted to 16 to 17° C. Thus, in step 3, the oxygen supply amount was controlled to be 0.28 volume %/h with respect to the volume of the dispersion in the reaction vessel under standard conditions (25° C., 101.3 kPa (absolute pressure)), and heating of the dispersion was started after 0.3 hours from the start of the nitrogen substitution operation in step 2. In step 2, the reduction ratio of the dissolved oxygen concentration was 69%, and the time required for the nitrogen substitution operation was 0.2 hours. In step 3, heating of the dispersion was started after 0.1 hour from the start of oxygen supply to the dispersion, the rate of temperature increase of the dispersion was 18.6° C. per hour. In step 4, the time required for the dehydration was 3.5 hours. In step 5, the time required for the evaporation was 18.1 hours in total.

The viscosity at 30° C. of the aqueous solution prepared by dissolving the obtained dispersion in water and setting the concentration of hydrophilic polymer particles at 1.0 mass % was 2070 mPa·s.

Example 9

In Example 9, the same operation as that of Example 7 was performed except that the oxygen supply amount in step 3 was 0.13 volume %/h, heating of the dispersion was started after 0.2 hours from the start of the nitrogen substitution operation in step 2, and the temperature of the dispersion in step 2 was adjusted to 27 to 28° C. In step 2, the reduction ratio of the dissolved oxygen concentration was 67%, and the time required for the nitrogen substitution operation was 0.15 hours. In step 3, heating of the dispersion was started after 0.05 hours from the start of oxygen supply to the dispersion, the rate of temperature increase of the dispersion was 16.4° C. per hour. In step 4, the time required for the dehydration was 4.8 hours. In step 5, the time required for the evaporation was 17.4 hours in total.

The viscosity at 30° C. of the aqueous solution prepared by dissolving the obtained dispersion in water and setting the concentration of hydrophilic polymer particles at 1.0 mass % was 2060 mPa·s.

Example 10

In Example 10, the same operation as that in Example 1 was performed except that the oxygen supply amount in step 3 was 0.67 volume %/h, and heating of the dispersion was started after 0.8 hours from the start of the nitrogen substitution operation in step 2. In step 2, the reduction ratio of the dissolved oxygen concentration was 79%, and the time required for the nitrogen substitution operation was 0.6 hours. In step 3, heating of the dispersion was started after 0.2 hours from the start of oxygen supply to the dispersion, the rate of temperature increase of the dispersion was 65.1° C. per hour.

The viscosity at 30° C. of the aqueous solution prepared by dissolving the obtained dispersion in water and setting the concentration of hydrophilic polymer particles at 1.0 mass % was 1650 mPa·s. In step 4, the time required for the dehydration was 7.5 hours. In step 5, the time required for the evaporation was 21.8 hours in total.

Example 11

In Example 11, the same operation as that of Example 7 was performed except that the hydrophobic solvent was normal hexane, the oxygen supply amount in step 3 was 0.21 volume %/h, and the temperature of the dispersion in step 2 was adjusted to 27 to 28° C. Thus, in step 3, heating of the dispersion was started after 0.3 hours from the start of the nitrogen substitution operation in step 2. In step 2, the reduction ratio of the dissolved oxygen concentration was 71%, and the time required for the nitrogen substitution operation was 0.2 hours. In step 3, heating of the dispersion was started after 0.1 hour from the start of oxygen supply to the dispersion, the rate of temperature increase of the dispersion was 16.1° C. per hour. In step 4, the time required for the dehydration was 5.0 hours. In step 5, the time required for the evaporation was 18.3 hours in total.

The viscosity at 30° C. of the aqueous solution prepared by dissolving the obtained dispersion in water and setting the concentration of hydrophilic polymer particles at 1.0 mass % was 1780 mPa·s.

Comparative Example 1

In Comparative Example 1, the same operation as that in Example 1 was performed except that the nitrogen substitution operation in step 2 was performed 10 times, the oxygen supply amount in step 3 was 0.58 volume %/h, and heating of the dispersion was started after 3.8 hours from the start of the nitrogen substitution operation in step 2. In step 2, the reduction ratio of the dissolved oxygen concentration was 87%, and the time required for the nitrogen substitution operation was 3.0 hours. In step 3, heating of the dispersion was started after 0.3 hours from the start of oxygen supply to the dispersion, the rate of temperature increase of the dispersion was 52.8° C. per hour. In step 4, the time required for the dehydration was 7.0 hours. In step 5, the time required for the evaporation was 31.8 hours in total.

The viscosity at 30° C. of the aqueous solution prepared by dissolving the obtained dispersion in water and setting the concentration of hydrophilic polymer particles at 1.0 mass % was 5330 mPa·s. A shampoo having a composition shown in Table 3 and prepared by using the dispersion including the obtained hydrophilic polymer particles, showed a high degree of friction feeling at a rinse. Thus, it is difficult to mix the dispersion including the hydrophilic polymer particles in shampoos.

Comparative Example 2

In Comparative Example 2, the same operation as that in Example 1 was performed except that step 2 was not performed and heating of the dispersion was started with an oxygen supply amount in step 3 of 0.65 volume %/h. In step 2, the reduction ratio of the dissolved oxygen concentration was 0%. In step 3, the rate of temperature increase of the dispersion was 42.9° C. per hour. In step 4, the time required for the dehydration was 6.8 hours. In step 5, the time required for the evaporation was 22.3 hours in total.

The viscosity at 30° C. of the aqueous solution prepared by dissolving the obtained dispersion in water and setting the concentration of hydrophilic polymer particles at 1.0 mass % was 1450 mPa·s. A shampoo having a composition shown in Table 3 and prepared by using the dispersion including the obtained hydrophilic polymer particles, leaves slimy feeling at a rinse. Thus, it is difficult to mix the dispersion including the hydrophilic polymer particles in shampoos.

Comparative Example 3

In Comparative Example 3, steps 1 to 5 were performed as follows:

(Step 1: Dispersion Preparation Step)

A 10-L reaction vessel was supplied with 4.5 kg of cyclohexane and 5.1 g of a dispersing agent (sucrose stearate). In addition, a 3-L monomer vessel was supplied with 0.15 kg of a 90% aqueous solution containing dimethylaminoethyl methacrylate diethylsulfate, 0.38 kg of N,N-dimethylacrylamide, 0.11 g of polyethylene glycol dimethacrylate, 0.73 kg of deionized water, and 2.5 g of a polymerization initiator (2,2'-azobis(2-amidinopropane) dihydrochloride).

Next, while cyclohexane and the dispersing agent were stirred in the reaction vessel, the aqueous-phase component including monomers and the polymerization initiator was supplied to the reaction vessel from the monomer vessel, and then the mixture was further stirred, thereby obtaining a solution mixture.

Subsequently, the solution mixture in the reaction vessel was heated to 27° C., and was mixed at 9000 rpm for 5 minutes with a homomixer (T.K. ROBO MICS produced by Tokushu Kika Kogyo Co., Ltd.), thereby preparing a dispersion.

While the obtained dispersion was stirred in the reaction vessel, the temperature of the dispersion was adjusted to 27 to 28° C.

(Step 2: Dissolved Oxygen Reduction Step)

Under the atmospheric pressure, a nitrogen gas was supplied to the dispersion from an upper space of the reaction vessel at a flow rate of 60 L per hour under standard conditions (25° C., 101.3 kPa (absolute pressure)) and the stirring was continued for 0.2 hours so that the dissolved oxygen concentration in the dispersion was reduced. The reduction ratio of the dissolved oxygen concentration in this step was 26%.

(Step 3: Polymerization Step)

After the reduction of the dissolved oxygen concentration had been confirmed, the stirring was continued under the atmospheric pressure, and heating of the dispersion was started after 0.3 hours from the start of introduction of a nitrogen gas in step 2 was started, i.e., reduction of the dissolved oxygen concentration. At this time, no oxygen was supplied to the reaction vessel. After the start of heating, the temperature of the dispersion in the reaction vessel was increased to 54 to 57° C., and polymerization reaction was performed for 40 minutes in this temperature range, thereby obtaining a dispersion in which hydrophilic polymer particles were dispersed. The rate of temperature increase of the dispersion was 41.7° C. per hour.

(Step 4: Dehydration Step)

After the polymerization reaction in step 3, the jacket temperature of the reaction vessel was kept at 95° C., and cyclohexane and water were evaporated and removed from the reaction vessel, thus performing dehydration. A fraction was obtained by condensing the vapor in a condenser, separating the condensed vapor into water and cyclohexane while allowing the vapor to stand. During the dehydration, the separated cyclohexane was continuously refluxed in the reaction vessel, whereas only water was caused to evaporate to be removed from the reaction vessel. The time required for the dehydration was 5.4 hours.

(Step 5: Solvent Substitution Step)

To the dispersion obtained in step 4, 0.65 kg of polyoxyethylene alkyl ether was added, the jacket temperature was set at 80° C., and the internal pressure of the vessel was reduced to 26.7 kPa (absolute pressure), thereby evaporating and removing cyclohexane.

At the time when it became impossible to observe evaporation of cyclohexane visually, a solution mixture of 0.13 kg of polyoxyethylene alkyl ether and 14.5 g of water was added, the jacket temperature was set at 80° C. again, and the internal pressure of the vessel was reduced to 40 kPa (absolute pressure), thereby performing second evaporation of cyclohexane. In this manner, a dispersion including 0.52 kg of hydrophilic polymer particles was obtained. The time required for the evaporation was 18.7 hours in total.

The viscosity at 30° C. of the aqueous solution prepared by dissolving the obtained dispersion in water and setting the concentration of hydrophilic polymer particles at 1.0 mass % was 1080 mPa·s.

Comparative Example 4

In Comparative Example 4, the same operation as that in Example 1 was performed except that the oxygen supply amount in step 3 was 0.94 volume %/h and heating of the dispersion was started after 0.9 hours from the start of the nitrogen substitution operation in step 2. In step 2, the reduction ratio of the dissolved oxygen concentration was 61%, and the time required for the nitrogen substitution operation was 0.7 hours. In step 3, the heating of the dispersion was started after 0.2 hours from the start of oxygen supply to the dispersion, and the rate of temperature increase of the dispersion was 43.1° C. per hour. In step 4, the time required for the dehydration was 7.2 hours. In step 5, the time required for the evaporation was 21.9 hours in total.

The viscosity at 30° C. of the aqueous solution prepared by dissolving the obtained dispersion in water and setting the concentration of hydrophilic polymer particles at 1.0 mass % was 1170 mPa·s.

Comparative Example 5

In Comparative Example 5, the same operation as that of Example 7 was performed except that step 3 was performed under the atmospheric pressure, no oxygen was supplied to the dispersion in the reaction vessel, and heating of the dispersion was started after 1.1 hours from the start of the nitrogen substitution operation in step 2. In step 2, the reduction ratio of the dissolved oxygen concentration was 81%, and time required for the nitrogen substitution operation was 0.8 hours. In step 3, the rate of temperature increase of the dispersion was 15.3° C. per hour. In step 4, the time required for the dehydration was 3.9 hours. In step 5, the time required for the evaporation was 26.1 hours in total.

The viscosity at 30° C. of the aqueous solution prepared by dissolving the obtained dispersion in water and setting the concentration of hydrophilic polymer particles at 1.0 mass % was 4190 mPa·s.

TABLE 1

| | Example | | | | | | | | | | |
|---|---|---|---|---|---|---|---|---|---|---|---|
| | 1 | 2 | 3 | 4 | 5 | 6 | 7 | 8 | 9 | 10 | 11 |
| Time from reduction of dissolved oxygen concentration in step 2 to start of heating of dispersion in step 3 (hours) | 2.6 | 1.7 | 1.0 | 0.9 | 1.6 | 1.1 | 0.3 | 0.3 | 0.2 | 0.8 | 0.3 |
| Oxygen supply amount relative to dispersion volume (volume %/hour) | 0.60 | 0.35 | 0.35 | 0.35 | 0.77 | 0.25 | 0.28 | 0.28 | 0.13 | 0.67 | 0.21 |
| Reduction ratio of dissolved oxygen concentration (%) | 83 | 89 | 77 | 64 | 82 | 60 | 61 | 69 | 67 | 79 | 71 |
| Dispersion temperature in step 2 (° C.) | 27-28 | 27-28 | 27-28 | 27-28 | 27-28 | 27-28 | 36-37 | 16-17 | 27-28 | 27-28 | 27-28 |
| Rate of temperature increase of dispersion in step 3 (° C./hour) | 50.8 | 46.9 | 47.8 | 45.0 | 43.4 | 46.3 | 15.3 | 18.6 | 16.4 | 65.1 | 16.1 |
| Hydrophilic polymer aqueous solution viscosity (mPa · s) | 3470 | 2660 | 2500 | 2180 | 1640 | 2760 | 1990 | 2070 | 2060 | 1650 | 1780 |
| Hydrophobic solvent | cyclehexane | cyclehexane | cyclehexane | cyclehexane | cyclehexane | cyclehexane | cyclehexane | cyclehexane | cyclehexane | cyclehexane | normal hexane |

TABLE 2

| | Comparative Example | | | | |
|---|---|---|---|---|---|
| | 1 | 2 | 3 | 4 | 5 |
| Time from reduction of dissolved oxygen concentration in step 2 to start of heating of dispersion in step 3 (hours) | 3.8 | — | 0.3 | 0.9 | 1.1 |
| The oxygen supply amount relative to dissolution volume (volume %/hour) | 0.58 | 0.65 | 0 | 0.94 | 0 |
| Reduction ratio of dissolved oxygen concentration (%) | 87 | 0 | 26 | 61 | 81 |
| Dispersion temperature in step 2 (° C.) | 27-28 | 27-28 | 27-28 | 27-28 | 27-28 |
| Rate of temperature increase of dispersion in step 3 (° C./hour) | 52.8 | 42.9 | 41.7 | 43.1 | 15.3 |

TABLE 2-continued

|  | Comparative Example | | | | |
|---|---|---|---|---|---|
|  | 1 | 2 | 3 | 4 | 5 |
| Hydrophilic polymer aqueous solution viscosity (mPa·s) | 5330 | 1450 | 1080 | 1170 | 4190 |
| Hydrophobic solvent | cycle hexane | cycle hexane | cycle hexane | cycle hexane | cycle hexane |

TABLE 3

| <Composition> | <mass %> |
|---|---|
| Polyoxyethylene(2)sodium lauryl ether sulfate [EMAL 270S produced by Kao Corporation] | 18.6 |
| Cocamidopropyl betaine [AMPHITOL 55AB produced by Kao Corporation] | 5.0 |
| Cocamido MEA [AMIZORU CME produced by Kawaken Fine Chemicals Co., Ltd.] | 0.3 |
| Dispersion including hydrophilic polymer particles | 0.6 |
| Dimethiconol [DC1785 produced by DOW CORNING Co., Ltd.] | 2.5 |
| PEARL CONC. [SA-M2 produced by Kao Corporation] | 5.0 |
| Perfume, methylparaben | proper quantity |
| Purified water | balance |
| Total | 100.0 |

INDUSTRIAL APPLICABILITY

The present invention is useful for a method for producing hydrophilic polymer particles.

The invention claimed is:

1. A method for producing hydrophilic polymer particles, the method comprising:
   step 1: preparing a dispersion in which an aqueous-phase component including hydrophilic monomers and a polymerization initiator is dispersed in an oil-phase component including a hydrophobic solvent having a solubility of 1 mass % or less in water at 25° C.;
   step 2: reducing a dissolved oxygen concentration of the dispersion prepared in step 1; and
   step 3: polymerizing the hydrophilic monomers in the aqueous phase by supplying oxygen to a reaction vessel and, while oxygen is being supplied, heating the dispersion whose dissolved oxygen concentration was reduced in step 2 in the reaction vessel so that a temperature of the dispersion increases, wherein
   a time from a start of reduction of the dissolved oxygen concentration of the dispersion in step 2 to a start of heating of the dispersion in step 3 is greater than or equal to 0.1 hour and less than or equal to 3.5 hours, and
   an amount of oxygen supplied to the reaction vessel in step 3 is greater than or equal to 0.02 volume % per hour and less than or equal to 0.9 volume % per hour with respect to a volume of the dispersion, under standard conditions of a temperature of 25° C. and an absolute pressure of 101.3 kPa.

2. The method of claim 1, wherein
   in step 3, a rate of temperature increase of the dispersion is greater than or equal to 5° C. per hour and less than or equal to 100° C. per hour.

3. The method of claim 1, wherein
   in step 2, a reduction ratio of the dissolved oxygen concentration of the dispersion is 40% or more, relative to a dissolved oxygen concentration of the dispersion at the start of reduction of the dissolved oxygen concentration.

4. The method of claim 1, wherein
   in step 2, the dissolved oxygen concentration of the dispersion is reduced by reducing an internal pressure of the reaction vessel storing the dispersion prepared in step 1 and then introducing an inert gas into the reaction vessel so that the internal pressure returns to a normal pressure.

5. The method of claim 1, wherein
   in step 1, the dispersion is prepared by dispersing the aqueous-phase component including the polymerization initiator in advance together with hydrophilic monomers in the oil-phase component including the hydrophobic solvent.

6. The method of claim 1, wherein
   in step 2, the temperature of the dispersion is greater than or equal to 0° C. and less than or equal to 50° C.

7. The method of claim 1, wherein
   in step 1, the oil-phase component includes a dispersing agent.

8. The method of claim 1, wherein
   in step 3, oxygen is supplied by using an oxygen-containing gas.

9. The method of claim 8, wherein
   an oxygen content of the oxygen-containing gas used in step 3 is greater than or equal to 1 volume % and less than or equal to 50 volume %, relative to the oxygen-containing gas.

10. The method of claim 1, wherein
    the hydrophilic polymer includes copolymer of vinyl monomers having cationic groups and/or a salt thereof, vinyl monomers having hydrophilic nonionic groups, and crosslinkable vinyl monomers having at least two reactive unsaturated groups in a molecule.

11. The method of claim 1, further comprising
    step 4: reducing a content of water by dehydrating the dispersion of hydrophilic polymer particles obtained in step 3.

12. The method of claim 11, further comprising
    step 5: substituting, by a substitution solvent, the hydrophobic solvent included in the dispersion of hydrophilic polymer particles dehydrated in step 4.

13. The method of claim 1, wherein
    the amount of oxygen supplied to the reaction vessel in step 3 is greater than or equal to 0.1 volume % per hour and less than or equal to 0.7 volume % per hour with respect to the volume of the dispersion, under standard conditions of a temperature of 25° C. and an absolute pressure of 101.3 kPa.

14. The method of claim 1, wherein
    the time from the start of reduction of the dissolved oxygen concentration of the dispersion in step 2 to the start of heating of the dispersion in step 3 is greater than or equal to 0.3 hour and less than or equal to 2.0 hours.

* * * * *